US009535076B2

(12) United States Patent
Kayed et al.

(10) Patent No.: US 9,535,076 B2
(45) Date of Patent: *Jan. 3, 2017

(54) METHODS AND COMPOSITIONS FOR ELICITING AN AMYLOID-SELECTIVE IMMUNE RESPONSE

(75) Inventors: Rakez Kayed, Galveston, TX (US); Charles G. Glabe, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 59 days.

This patent is subject to a terminal disclaimer.

(21) Appl. No.: 13/055,899

(22) PCT Filed: Jul. 27, 2009

(86) PCT No.: PCT/US2009/051863
§ 371 (c)(1),
(2), (4) Date: Apr. 18, 2011

(87) PCT Pub. No.: WO2010/011999
PCT Pub. Date: Jan. 28, 2010

(65) Prior Publication Data
US 2011/0250217 A1    Oct. 13, 2011

Related U.S. Application Data

(63) Continuation-in-part of application No. 10/572,001, filed as application No. PCT/US2004/029946 on Sep. 13, 2004, now abandoned, which is a continuation-in-part of application No. 10/527,678, filed as application No. PCT/US03/28829 on Sep. 12, 2003.

(60) Provisional application No. 61/083,810, filed on Jul. 25, 2008, provisional application No. 60/502,326, filed on Sep. 12, 2003, provisional application No. 60/410,069, filed on Sep. 12, 2002.

(51) Int. Cl.
| A61K 39/00 | (2006.01) |
| A61K 47/02 | (2006.01) |
| A61K 47/48 | (2006.01) |
| G01N 33/68 | (2006.01) |
| C07K 7/08 | (2006.01) |
| C07K 16/18 | (2006.01) |

(52) U.S. Cl.
CPC ....... *G01N 33/6896* (2013.01); *A61K 39/0007* (2013.01); *C07K 7/08* (2013.01); *C07K 16/18* (2013.01); *A61K 2039/55505* (2013.01); *A61K 2039/55566* (2013.01); *A61K 2039/60* (2013.01); *G01N 2800/2821* (2013.01)

(58) Field of Classification Search
CPC .............. A61K 39/0007; A61K 2039/55505; A61K 2039/55566; A61K 2039/60; A61K 2039/6081; A61K 2039/6031; A61K 47/02; A61K 47/48015; A61K 47/48861; C07K 17/14; C07K 2319/00; C07K 2319/55; C12N 2531/00
See application file for complete search history.

(56) References Cited

U.S. PATENT DOCUMENTS

| 5,057,540 A | 10/1991 | Kensil et al. |
| 5,178,882 A * | 1/1993 | Kossovsky ............ A61K 39/12 424/204.1 |
| 5,314,813 A | 5/1994 | Peterson et al. |
| 5,593,846 A | 1/1997 | Schenk et al. |
| 5,612,486 A | 3/1997 | McConlogue et al. |
| 5,688,651 A | 11/1997 | Solomon |
| 6,114,133 A | 9/2000 | Seubert et al. |
| 6,743,427 B1 | 6/2004 | Schenk |
| 6,750,324 B1 | 6/2004 | Schenk et al. |
| 6,761,888 B1 | 7/2004 | Schenk |
| 6,787,637 B1 | 9/2004 | Schenk |
| 7,179,463 B2 * | 2/2007 | Lannfelt et al. ........... 424/139.1 |
| 2002/0187157 A1* | 12/2002 | Jensen et al. ............... 424/185.1 |
| 2003/0068316 A1* | 4/2003 | Klein et al. ................ 424/130.1 |
| 2003/0185835 A1* | 10/2003 | Braun ........................ 424/184.1 |
| 2006/0210605 A1 | 9/2006 | Chang et al. |
| 2006/0280733 A1* | 12/2006 | Kayed et al. ............... 424/133.1 |

FOREIGN PATENT DOCUMENTS

| EP | 0526511 B1 | 5/1997 |
| GB | 2220211 A | 1/1990 |
| WO | WO90/07861 A1 | 7/1990 |
| WO | WO90/14837 A1 | 12/1990 |
| WO | WO91/10741 A1 | 7/1991 |
| WO | WO91/17271 A1 | 11/1991 |
| WO | WO92/01047 A1 | 1/1992 |

(Continued)

OTHER PUBLICATIONS

Tjernberg LO et al. Assembling amyloid fibrils from designed structures containing a significant amyloid beta-peptide fragment. Biochem. J. Aug. 2002; 366:343-351.*
Walsh DM et al. Amyloid beta-protein fibrillogenesis: Structure and biological activity of protofibrillar intermediates. J. Biol. Chem. 1999; 274(36):25945-25952.*
O'Nuallain B & Wetzel R. (Feb. 2002) Conformational Abs recognizing a generic amyloid fibril epitope. Proc. Natl. Acad. Sci. USA, 99(3):1485-1490.*
Tjernberg LO et al. (2002) Assembling amyloid fibrils from designed structures containing a significant amyloid b-peptide fragment. Biochem. J. 366:343-351.*
Broome BM et al. (2000) Nature disfavors sequences of alternating polar and non-polar amino acids: implications for amyloidogenesis. J. Mol. Biol. 296:961-968.*

(Continued)

*Primary Examiner* — Kimberly A. Ballard
(74) *Attorney, Agent, or Firm* — Robert D. Buyan; Stout, Uxa & Buyan, LLP

(57) ABSTRACT

The present invention involves methods and compositions for treating, preventing, and diagnosing amyloid-associated diseases and conditions, as well as methods and compositions for making antigens that elicit antibodies which selectively or specifically bind amyloid prefibrillar oligomers or protofibrillar aggregates over monomers or fibrils of the same amyloid.

12 Claims, 6 Drawing Sheets

(56) References Cited

FOREIGN PATENT DOCUMENTS

| WO | WO93/12227 A1 | 6/1993 |
|---|---|---|
| WO | WO97/17613 A1 | 5/1997 |
| WO | WO97/17614 A1 | 5/1997 |
| WO | WO99/27944 A1 | 6/1999 |
| WO | WO 0072880 A2 * | 12/2000 |
| WO | WO2004/024090 A1 | 3/2004 |
| WO | WO2005/025516 A2 | 3/2005 |
| WO | WO 2005/123775 A1 | 12/2005 |

OTHER PUBLICATIONS

West MW et al. (1999) De novo amyloid proteins from designed combinatorial libraries. Proc. Natl. Acad. Sci. USA, 96:11211-11216.*

SAFC Live Blog, Producing KLH for Vaccine Use: SAFC's Dave Backer discusses the strategic marketing and sales agreement with Stellar Biotechnologies. Posted Aug. 3, 2011.*

Broome BM et al. Nature disfavors sequences of alternating polar and non-polar amino acids: Implications for amyloidogenesis. J. Mol. Biol. 2000, 296:961-968.*

Kametekar et al. Protein design by binary patterning of polar and nonpolar amino acids. Science, 1993, 262:1680-1685.*

West et al. De novo amyloid proteins from designed combinatorial libraries. Proc. Natl. Acad. Sci. USA, 1999, 96:11211-11216.*

Xiong et al. Periodicity of polar and nonpolar amino acids is the major determinant of secondary structure in self-assembling oligomeric peptides. Proc. Natl. Acad. Sci. USA, 1995, 92:6349-6353.*

Lashuel, Hilal A. et al., Neurodegenerative disease: Amyloid pores from pathogenic mutations, Nature, Jul. 18, 2002, p. 291, vol. 418.

O'Nuallain, Brian et al., Conformational Abs recognizing a generic amyloid fibril epitope, PNAS, Feb. 5, 2002, pp. 1485-1490, vol. 99, No. 3.

Goldsteins, Gundars, et al., Exposure of cryptic epitopes on transthyretin only in amyloid and in amyloidogenic mutants, PNAS, Mar. 16, 1999, pp. 3108-3113, vol. 96, No. 6.

Hrncic, Rudi et al., Antibody-mediated resolution of light chain associated amyloid deposits, American Journal of Pathology, Oct. 2000, pp. 1239-1246, vol. 157, No. 4.

Glabe, Charles, Intracellular mechanisms of amyloid accumulation and pathogensis in Alzheimer's disease, Journal of Molecular Neuroscience, 2001, pp. 137-145, vol. 17.

El-Agnaf, Omar, M.A., et al., Soluble oligomers for the diagnosis of neurodegenerative disease, The Lancet, Aug. 2003, pp. 461-462,vol. 2.

Yang, Austin J. et al., Intracellular accumulation of insoluble, newly synthesized ABn-42 in amyloid precursor protein-transfected cells that have been treated with AB1-42, The Journal of Biological Chemistry, Jul. 16, 1999, pp. 20650-20656, vol. 274, No. 29.

Kayed, Rakez, et al., Common structure of soluble amyloid oligomers implies common mechanism of pathogensis, Science, Apr. 18, 2003, pp. 486-489, vol. 300.

Hardy, John et al., The amyloid hypothesis of Alzheimer's disease: progress and problems on the road to therapeutics, Science, Jul. 19, 2002, pp. 353-356, vol. 297.

Lansbury, Peter T., Jr., Evolution of amyloid: what normal protein folding may tell us about fibrillogenesis and disease, PNAS, Mar. 30, 1999, pp. 3342-3344, vol. 96, No. 7.

Bunnell, William, L., et al., g-Secretase cleavage is distinct from endoplasmic reticulum degradation of the transmembrane domain of the amyloid precursor protein, The Journal of Biological Chemistry, Nov. 27, 1998, pp. 31947-31955, vol. 273, No. 48.

Torok, Marianna, et al., Structural and dynamic features of Alzheimer's AB peptide in amyloid fibrils studied by site-directed spin labeling, The Journal of Biological Chemistry, Oct. 25, 2002, pp. 40810-40815, vol. 277, No. 43.

Garzon-Rodriguez, William, et al., A conformation change in the carboxyl terminus of Alzheimer's AB(1-40) accompanies the transition from dimer to fibril as revealed by fluorescence quenching analysis, The Journal of Biological Chemistry, Jul. 28, 2000, pp. 22645-22649, vol. 275, No. 30.

Garzon-Rodriguez, William, et al., Soluble amyloid AB-(1-40) exists as a stable dimer at low concentrations, The Journal of Biological Chemistry, Aug. 22, 1997, pp. 21037-21044, vol. 272, No. 34.

Soreghan, Brian, et al., Surfactant properties of Alzheimer's AB peptides and the mechanism of amyloid aggregation, The Journal of Biological Chemistry, Nov. 18, 1994, pp. 28551-28554, vol. 269, No. 46.

Lambert, Mary P., et al., Vaccination with soluble AB oligomers generates toxicity-neutralizing antibodies, Journal of Neurochemistry, 2001, pp. 595-605, vol. 79.

Jiang, Haixiang, et al., B-Amyloid activates complement by binding to a specific region of the collagen-like domain of the C1qA chain, Journal of Immunology, 1994, pp. 5050-5059, vol. 152.

Lambert, M.P. et al., Diffusible, nonfibrillar ligands derived from Abeta1-42 are potent central nervous system neurotoxins, PNAS, May 1998, pp. 6448-6453, vol. 95.

Yang, Austin Y. et al., Intracellular AB1-42 Aggregates Stimulate the Accumulation of Stable, Insoluble Amyloidogenic Fragments of the Amyloid Precursor Protein in Transfected Cells, The Journal of Biological Chemistry, Jun. 16, 1995, pp. 14786-14792, vol. 270, No. 24.

Pearson, William R. et al, Improved tools for biological sequence comparison, PNAS, Apr. 1988, pp. 2444-2448, vol. 85.

Bucciantini, Monica et al., Inherent toxicity of aggregates implies a common mechanism for protein misfolding diseases, Nature, Apr. 4, 2002, pp. 507-511, vol. 416.

McLean, Catriona A. et al., Soluble pool of AB amyloid as a determinant of severity of neurodegeneration in Alzheimer's disease, Annals of Neurology, 1999, pp. 860-866, vol. 46.

Cevc, Gregor et al., Ultraflexible vesicles, transferosomes, have an extremely low pore penetration resistance and transport therapeutic amounts of insulin across the intact mammalian skin, Biochimica et Biophysica Acta, 1998, pp. 201-215, vol. 1368.

Chang, Jennie C.C. et al., Adjuvant activity of incomplete Freund's adjuvant, Advanced Drug Delivery Reviews, 1998, pp. 173-186, vol. 32.

Chartier-Harlin, Marie-Christine et al., Early onset Alzheimer's disease caused by mutations at codon 717 of the B-amyloid precursor protein gene, Nature, Oct. 31, 1991, pp. 844-846, vol. 353.

Lue, Lih-Fen et al., Soluble Amyloid B peptide concentration as a predictor of synaptic change in Alzheimer's disease, American Journal of Pathology, 1999, pp. 853-862, vol. 155.

Hanes, Justin et al., New advances in microsphere-based single dose vaccines, Advanced Drug Delivery Reviews, 1997, pp. 97-119, vol. 28.

Mullan, Mike et al., A pathogenic mutation for probable Alzheimer's disease in the APP gene at the N-terminus of B-amyloid, Nature Genetics, Aug. 1992, pp. 345-347, vol. 1.

Glenn, Gregory M. et al., Skin immunization made possible by cholera toxin, Nature, Feb. 26, 1998, pp. 851, vol. 391.

Goate, Alison et al., Segregation of a missense mutation in the amyloid precursor protein gene with familial Alzheimer's disease, Nature, Feb. 21, 1991, pp. 704-706, vol. 349.

Hardy, John, Amyloid, the presenilins and Alzheimer's disease, Trends in Neurosciences, 1997, pp. 154-159, vol. 20.

Hartley, Dean M. et al., Protofibrillar Intermediates of Amyloid B-protein induce acute electrophysiological changes and progressive neurotoxicity in cortical neurons, The Journal of Neuroscience, Oct. 15, 1999, pp. 8876-8884, vol. 10, No. 20.

Henikoff, Steven et al., Amino acid substitution matrices from protein blocks, PNAS, Nov. 1992, pp. 10915-10919, vol. 89.

Queen, Cary et al., A humanized antibody that binds to the interleukin 2 receptor, PNAS, Dec. 1989, pp. 10029-10033, vol. 86.

Stoute, Jose A. et al., A preliminary evaluation of a recombinant circumsporozoite protein vaccine against plasmodium falciparum malaria, The New England Journal of Medicine, Jan. 9, 1997, pp. 86-91, vol. 336, No. 2.

(56) References Cited

OTHER PUBLICATIONS

Kuo, Yu-Min et al., Water soluble AB(N-40, N-42) oligomers in normal and Alzheimer disease brains, The Journal of Biological Chemistry, Feb. 23, 1996, pp. 4077-4081, vol. 271, No. 8.

Knauer, Mary F. et al., Intracellular accumulation and resistance to degradation of the Alzheimer amyloid A4/B protein, PNAS, Aug. 1992, pp. 7437-7441, vol. 89.

Kayed & Glabe, "Conformation—Dependent Anti-Amyloid Oligomer Antibodies," Methods in Enzymology, vol. 413, Copyright 2006, Elsevier Inc., pp. 326-344.

Kayed et al., "Permeabilization of Lipid Bilayers is a Common Conformation-dependent Activity of Soluble Amyloid Oligomes in Protein Misfolding Diseases," J. Biol. Chem. vol. 279, No. 45:46363-6 (2004).

International Search Report dated May 23, 2005 in International Application No. PCT/US04/29946.

Supplemental European Search Report in European Patent Application No. EP 04788729, dated Sep. 14, 2009.

\* cited by examiner

Antigen Preparation

Dot blot; 10 min exposure

Standard Strips; 10 min

| 1 | 2. | 3 | 4 | 5 | 6 |
|---|---|---|---|---|---|
| AB Sol | AB Oligo. | AB Fib | Syn. Oligo | Prion Oligo | Insulin Oligo |

```
                         SEQUENCE LISTING

<160> NUMBER OF SEQ ID NOS: 15

<210> SEQ ID NO 1
<211> LENGTH: 40
<212> TYPE: PRT
<213> ORGANISM: Unknown
<220> FEATURE:
<223> OTHER INFORMATION: Description of Unknown: ABeta40 amyloid
      peptide

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 42
<212> TYPE: PRT
<213> ORGANISM: Unknown
<220> FEATURE:
<223> OTHER INFORMATION: Description of Unknown: ABeta42 amyloid
      peptide

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 37
<212> TYPE: PRT
<213> ORGANISM: Homo sapiens

<400> SEQUENCE: 3

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35
```

<210> SEQ ID NO 4
<211> LENGTH: 21
<212> TYPE: PRT
<213> ORGANISM: Homo sapiens

<400> SEQUENCE: 4

```
Lys Thr Asn Met Lys His Met Ala Gly Ala Ala Ala Ala Gly Ala Val
1               5                   10                  15

Val Gly Gly Leu Gly
            20
```

<210> SEQ ID NO 5
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Lys Lys Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln Gln
            20                  25                  30

Gln Gln Gln Gln Gln Gln Gln Gln Gln Lys Lys
            35                  40
```

<210> SEQ ID NO 6
<211> LENGTH: 147
<212> TYPE: PRT
<213> ORGANISM: Homo sapiens

<400> SEQUENCE: 6

```
Met Lys Ala Leu Ile Val Leu Gly Leu Val Leu Leu Ser Val Thr Val
1               5                   10                  15

Gln Gly Lys Val Phe Glu Arg Cys Glu Leu Ala Arg Thr Leu Lys Arg
            20                  25                  30

Leu Gly Met Asp Gly Tyr Arg Gly Ser Leu Ala Asn Trp Met Cys Leu
        35                  40                  45

Ala Lys Trp Glu Ser Gly Tyr Asn Thr Arg Ala Thr Asn Tyr Asn Ala
    50                  55                  60

Gly Asp Arg Ser Thr Asp Tyr Gly Ile Phe Gln Ile Asn Ser Arg Tyr
65                  70                  75                  80

Trp Cys Asn Asp Gly Lys Thr Pro Gly Ala Val Asn Ala Cys His Leu
                85                  90                  95

Ser Cys Ser Ala Leu Leu Gln Asp Asn Ile Ala Asp Ala Val Ala Cys
            100                 105                 110

Ala Lys Arg Val Val Arg Asp Pro Gln Gly Ile Arg Ala Trp Val Ala
        115                 120                 125

Trp Arg Asn Arg Cys Gln Asn Arg Asp Val Arg Gln Tyr Val Gln Gly
    130                 135                 140

Cys Gly Val
145
```

<210> SEQ ID NO 7
<211> LENGTH: 110
<212> TYPE: PRT
<213> ORGANISM: Homo sapiens -continued

<400> SEQUENCE: 7

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 8
<211> LENGTH: 147
<212> TYPE: PRT
<213> ORGANISM: Homo sapiens

<400> SEQUENCE: 8

Met Ala Ser His Arg Leu Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Glu
145

<210> SEQ ID NO 9
<211> LENGTH: 140
<212> TYPE: PRT
<213> ORGANISM: Homo sapiens

<400> SEQUENCE: 9

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr

```
                    50                  55                  60
Asn Val Gly Gly Ala Val Val Thr Gly Val Thr Ala Val Ala Gln Lys
 65                  70                  75                  80

Thr Val Glu Gly Ala Gly Ser Ile Ala Ala Thr Gly Phe Val Lys
                 85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
        130                 135                 140

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Phe Ile Tyr Leu Ile Phe Val Ser Ser His Leu Tyr Ser Thr Ser Leu
 1               5                  10                  15

Leu Tyr His Thr
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Tyr Leu Ile His Val His Ile Ile Thr Ile Tyr His Ile Ser Ile
 1               5                  10                  15

Tyr Tyr Ile Val
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Phe His Val Thr Val Tyr Leu Ser Leu Ser Phe Thr Phe Ser Leu
 1               5                  10                  15

Ser Phe Ser Val
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13
```

-continued

```
Thr Ile Tyr Phe Tyr Phe Tyr Phe Tyr Leu Thr Leu His Phe Tyr Phe
1               5                   10                  15

Thr Ile Ser Ile
            20

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 14

His His His His His His
1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gly Asp Ser
1
```

METHODS AND COMPOSITIONS FOR ELICITING AN AMYLOID-SELECTIVE IMMUNE RESPONSE

RELATED APPLICATION

This patent application is a 35 U.S.C. §371 national stage of PCT International Patent Application No. PCT/US09/051863 filed Jul. 27, 2009, which claims priority to U.S. Provisional Patent Application No. 61/083,810 filed Jul. 25, 2008, the entire disclosure of which is expressly incorporated herein by reference. Additionally, this patent application is a continuation in part of a) copending U.S. patent application Ser. No. 10/527,678 filed May 9, 2006, which is a 35 U.S.C. §371 national stage of PCT International Patent Application No. PCT/US2003/028829 filed Sep. 12, 2003, which claims priority to U.S. Provisional Patent Application No. 60/410,069 filed Sep. 12, 2002 and b) copending U.S. patent application Ser. No. 10/572,001 filed Dec. 21, 2006, which is a 35 U.S.C. §371 national stage of PCT International Patent Application No. PCT/US2004/029946 filed Sep. 13, 2004, which claims priority to U.S. Provisional Patent Application No. 60/502,326 filed Sep. 12, 2003.

SEQUENCE LISTING

The instant application contains a Sequence Listing which has been submitted in ASCII format via EFS-Web and is hereby incorporated by reference in its entirety. Said ASCII copy, created on Jun. 2, 2011, is named UCIVN082.txt and is 9,302 bytes in size.

FIELD OF THE INVENTION

The invention relates generally to the fields of medicine, immunology and protein biochemistry and more particularly to certain antigenic compositions, methods, and antibodies that are useful in the diagnosis, treatment and/or modeling of amyloid-associated diseases, including amyloid-like associated conditions.

BACKGROUND OF THE INVENTION

Many biological functions come about, at least in part, due to the ability of proteins to adopt various sequence-dependent structures. However, particularly, although not exclusively, with regard to neural functions, certain proteins can sometimes form aberrant, misfolded, aggregates known as amyloid oligomers and amyloid fibrils following expression of the protein. These amyloid aggregates are associated with and thought to be involved in the pathogenesis of various amyloid diseases of genetic, infectious and/or spontaneous origin, including spongiform encephalopathies, Alzheimer's disease, Parkinson's disease, type II diabetes, Creutzfeldt-Jakob disease, Huntington's disease, possibly macular degeneration, various prion diseases and numerous others. In at least some of these amyloid diseases, the formation of amyloid oligomers precedes and appear to lead to the development of amyloid fibril plaques.

Amyloid peptides are the principal constituent of amyloid plaques. In the case of Alzheimer's disease ("AD"), the peptides are termed Aβ or β-amyloid peptide. Aβ peptide is an internal proteolytic fragment of 39 to 43 amino acids of amyloid precursor protein (APP). The normal function of full-length APP is not definitively known, but it is thought to be associated with neuronal development. Aβ monomers are soluble and appear to be harmless in solution, but undergo a major conformational change at sufficiently high concentration, and thereafter form amyloid oligomers or fibrils that deposit within neurons or outside the neurons.

Several mutations within the APP protein have been correlated with the presence of AD. See, for example, Goate et al., *Nature*, (1991) 349, 704 (valine to isoleucine); Chartier Harlan et al., *Nature* (1991)353, 844 (valine to glycine); Murrell et al. *Science* (1991) 254, 97 (valine to phenylalanine); Mullan et al., *Nature Genet.* (1992) 1, 345 (a double mutation changing lysine$_{595}$-methionine$_{596}$ to asparagine$_{595}$-leucine$_{596}$). Such mutations are thought to cause AD by producing an increased or altered processing of APP to Aβ. In particular, the processing of APP resulting in accumulation of the longer forms of Aβ, for example, A1-42 and A1-43 is thought to be important in the cause of AD. Mutations in other genes, such as the presenilin genes PS1 and PS2, are thought to indirectly affect processing of APP resulting in production of the long form of Aβ. See, for example, Hardy, *TINS* (1997) 20, 154.

European Patent Publication EP 526,511 (McMichael) and PCT International Patent Publication WO/9927944 (Schenk) have described the administration of Aβ to patients for the treatment or prevention of Alzheimer's. However, although active immunization of Aβ to transgenic mice produces apparent benefits, the extension of this approach to AD patients has resulted in undesirable inflammation of the central nervous system in some of the subjects. See Hardy, D. J. Selkoe (2002) *Science* 297, 353-356.

Soluble Aβ includes Aβ monomers as well as soluble aggregations of such monomers referred to as "oligomers" or "prefibrillar oligomers" or "protofibrillar aggregates". These oligomers or prefibrillar oligomers or protofibrillar aggregates may eventually lead to the development of amyloid fibrils. Soluble Aβ content of the human brain is better correlated with the severity of AD than is the accumulation of amyloid plaques. See, for example, Y. M. Kuo et al. (1996) *J. Biol. Chem.* 271, 4077-4081; C. A. McLean et al. (1999) *Annals of Neurology* 46, 860-6; L. F. Lue et al. (1999) *American Journal of Pathology* 155, 853-862. In addition, recent reports suggest that the toxicity of Aβ and other amyloidogenic proteins lies not in the soluble monomers or insoluble fibrils that accumulate, but rather in the oligomers or oligomer prefibrillar oligomer or protofibrillar aggregates. See, for example, Hartley et al. (1999), *Journal of Neuroscience* 19, 8876-8884; Lambert et al., *Proceedings of the National Academy of Sciences of the United States of America* (1998) 95, 6448-53; and Bucciantini et al., *Nature* (2002) 416, 507-511; and Hartley et al. *Nature* (2002) 418, 291. Taken together, these results indicate that the appearance of oligomers or prefibrillar oligomers or protofibrillar aggregates may be considerably more pathologically significant than of other forms of the amyloid peptides and therefore may be a more desirable target in the prevention or curing of amyloid diseases such as AD.

There is therefore a need for the development of antigens capable of producing antibodies which selectively or specifically bind to and/or sequester the toxic form of amyloid, thereby inhibiting the pathogenesis, or slowing the progression of amyloid diseases. In addition, such antigens, may be useful in designing and purifying such antibodies. Further, therapeutic agents comprising at least one such antibody may be useful and a prophylactic against the development of the symptoms of AD, such as, without limitation, loss of memory (amnesia), language impairment (aphasia), impairment of skilled movements (apraxia), recognition (agnosia)

and decision making and planning functions characteristic of the frontal lobe of the brain, and well as the symptoms of other amyloid diseases.

SUMMARY OF THE INVENTION

The present invention provides antigens useful for producing antibodies which selectively or specifically bind soluble Aβ peptide oligomers and do not bind monomeric Aβ or soluble or insoluble Aβ fibrils. Also, these antibodies selectively or specifically recognize soluble amyloid peptide aggregates produced from the other types of amyloidogenic peptides and proteins examined herein while not binding to the corresponding low molecular weight amyloid peptides, fibrils or the native structure of the amyloidogenic protein.

In particular, the present invention exploits the discovery that peptides constructed from random peptide sequences, or translated from nucleic acids encoding such sequences, selected or designed for their tendency to form β-sheet oligomers, when used to construct antigens described herein, give rise to the production of antibodies that are able to bind soluble amyloid peptide aggregates from a variety of different amyloid proteins, including disease-related amyloids and peptides with selectivity over soluble amyloid monomers and insoluble amyloid fibrils. It is understood that the term "random", when used to describe the amino acid sequences of the antigenic peptides of the present invention, means that amino acids are randomly chosen from a pool of those amino acids having a high probability of forming beta sheets and low alpha helix probability. The polar amino acids selected were threonine, tyrosine, serine and histidine. The Non-polar amino acids selected were isoleucine, valine, phenylalanine and leucine. An equal number of polar and non-polar amino acids were selected to minimize the possible solubility problems of hydrophobic peptides. Although 8 total amino acids out of 20 were used, oligomers could be made from peptides containing all 20 amino acids.

In one embodiment, the antibodies produced in response to vaccination with these random peptide epitopes of the present invention bind soluble Aβ peptide oligomers with selectivity over soluble Aβ monomers and Aβ fibrils. Thus, in accordance with the present invention, there are provided isolated compositions, for example, antigenic compositions, which include an epitope, for example, a conformational epitope, antigenically similar to, or even indistinguishable from, that of a soluble oligomer or prefibrillar oligomer prefibrillar oligomer or protofibrillar aggregate that forms in a human or animal and contributes to amyloid fibril formation and disease pathology. Moreover, despite the fact that antibodies made using such epitopes as an immunogen will recognize soluble aggregates of a given amyloid peptide monomer, the primary amino acid sequence of such epitopes may be, and usually is, different from that found in the contiguous primary sequence of any particular naturally occurring amyloid peptide monomer. Additionally, these random sequences display minimal sequence identity with any naturally occurring protein in humans or vertebrate animals.

Thus, amyloid fibrils are or may be free of the epitopes, or substantially free of the epitopes, of the present compositions. In addition, amyloid peptide monomers may be free of the epitopes or substantially free of the epitopes of the present compositions. Naturally occurring natively folded proteins may be free or the epitopes or substantially free of the epitopes of the present compositions. Also provided herein are compositions which include antibodies which bind to the epitopes described herein.

In accordance with the invention, in some embodiments, the epitope compositions may comprise synthetic epitopes.

Further in accordance with the invention, in some embodiments, the epitope compositions may comprise epitopes made by recombinant technology and expressed heterologously by translation from nucleic acids in vivo or in vitro.

Still further in accordance with the invention, in some embodiments, the compositions may comprise pharmaceutical compositions such as vaccines.

Still further in accordance with the invention, the compositions may include a peptide or a protein that may be conformationally constrained. The peptides may be synthetic or made using recombinant technology and expressed heterologously by translation from nucleic acids in vivo or in vitro. In one embodiment, the peptide is selected from the group consisting of SEQ ID NO. 10, SEQ ID NO. 11, SEQ ID NO. 12, SEQ ID NO. 13, and mixtures thereof.

Still further in accordance with the invention, the compositions may be supported by a surface which may be of any shape including curved or flat. In one useful embodiment, the surface comprises solid matter. The surface may be a film, a particle (including irregular particles, and shaped particles such as spheres, microspheres, nanospheres and the like) or a sheet. In one embodiment, the surface is functionally modified, for example, functionally modified allowing for the formation of self assembled peptide monolayers. In addition, the surface may comprise a protein comprising, for example, a β-sheet structure. In one embodiment, peptides are bound to the support surface. For example, peptides may be chemically bonded to the support surface. Chemical bonds include ionic bonds, hydrogen bonds, covalent bonds and van der Waals attraction. In one particularly useful embodiment, peptides may be chemically bonded to the support surface using a covalent bond. The compositions may comprise a linker moiety effective to attach the peptides to the surface. The linkers may include, without limitation, streptavidin, hydrocarbon moieties, such as hydrocarbon chains, including, but not limited to, citrate, HS—$(CH_2)_n$—COOH, HS—$(CH_2)_n$—$NH_2$, HS—$(CH_2)_n$—OH, HS—$(CH_2)_n$—COOR, phosphoramide—$NH_2$, cyclic or acidic disulfide-R—COOH, cyclic or acidic disulfide-R—$NH_2$, $Si(OCH_3)_3$—R—$NH_2$, $Si(OCH_3)_3$—R—COOH and -maleimide. The support may comprise any suitable material including, but not limited to, gold, zinc, cadmium, tin, titanium, silver, selenium, gallium, indium, arsenic, silicon, mixtures thereof or combinations thereof.

Still further in accordance with the invention, oligomer or prefibrillar oligomer prefibrillar oligomer or protofibrillar aggregates as described herein may have a molecular weight in a range of about 10 kDa to about 100,000,000 kDa. In one embodiment, the oligomer prefibrillar oligomer or protofibrillar aggregate comprises five monomers. In another embodiment, the oligomer or prefibrillar oligomer prefibrillar oligomer or protofibrillar aggregate comprises eight monomers. The oligomer or prefibrillar oligomer prefibrillar oligomer or protofibrillar aggregate is present in a human or animal having a disease characterized by amyloid deposits and may comprise a toxic species. The invention provides for antibodies which may be effective to reduce the toxicity of oligomer or prefibrillar oligomer prefibrillar oligomer or protofibrillar aggregates.

Still further in accordance with the invention, the oligomer or prefibrillar oligomer prefibrillar oligomer or protofibrillar aggregate is present in a human or animal having a disease characterized by amyloid deposits. For example, the disease may be Alzheimer's, early onset Alzheimer's associated with Down's syndrome, SAA amyloidosis, hereditary Icelandic syndrome, multiple myeloma, and spongiform encephalopathies (such as bovine spongiform encephalopathy (BSE), mad cow disease, sheep scrapie, and mink spongiform encephalopathy), Parkinson's disease, Huntington's disease, amyotropic lateral sclerosis, Creutzfeld Jakob disease, Gerstmann-Straussler-Scheinker syndrome, kuru, fatal familial insomnia, chronic wasting syndrome, familial amyloid polyneuropathy, frontotemporal dementia, type II diabetes, systemic amyloidosis, serum amyloidosis, British familial dementia, Danish familial dementia, macular degeneration, glaucoma, cerebrovascular amyloidosis, a prion disease or another amyloid disease.

Still further in accordance with the invention, there are provided methods of preventing or treating a disease or condition in a human or animal subject, the disease or condition being characterized by the presence of amyloid deposits. The methods may include administering to the subject a therapeutically effective or preventative amount of a composition. In one embodiment, the method includes inducing an immune response against one or more conformational epitope described herein.

Still further in accordance with the invention, there are provided methods of preventing or treating a disease or condition characterized by amyloid deposits in a human or animal which include causing an antibody to bind to a conformational epitope characteristic of a soluble oligomer or prefibrillar oligomer prefibrillar oligomer or protofibrillar aggregate that forms in a human or animal and contributes to fibril formation. In one embodiment, the present methods include administering an antibody that selectively or specifically binds to a conformational epitope comprising a peptide having a random amino acid sequence characteristic of a soluble oligomer or prefibrillar oligomer prefibrillar oligomer or protofibrillar aggregate. The composition may be administered by intraspinal, intrathecal, oral, transdermal, pulmonary, intravenous, subcutaneous, intramuscular, intranasal, rectal, sublingual or buccal administration.

Still further in accordance with the invention, there are provided methods of making an antibody which may include administering to a human or animal a composition of the invention comprising an epitope that selectively or specifically binds to a soluble oligomer or prefibrillar oligomer prefibrillar oligomer or protofibrillar aggregate. The method may also include recovering the resulting antibody from the human or animal.

Still further in accordance with the invention there are provided methods of making polyclonal or monoclonal antibodies comprising isolating serum or cells, such as B-cells from the spleen or lymph nodes, of a mammal such as a rabbit or mouse that has been immunized using a constrained, prefibrillar oligomer epitope of the present invention. The polyclonal serum may be enriched for antibodies and used. If monoclonal antibodies are desired, the isolated B-cells are then fused with myeloma cells from a cell culture that has lost the ability to make antibodies using a cell membrane permeability-enhancing agent such as, without limitation, polyethylene glycol (PEG), a virus, or a technique such as electroporation. The fused hybridoma cells can then be isolated by cloning and selected clones of cells grown in culture and tested for the production of antibodies and the specificity of the monoclonal antibodies produced thereby.

Still further in accordance with the invention, there are provided methods of diagnosing a disease characterized by amyloid deposits which include combining tissue or fluid from a human or animal patient and an antigenic composition of the invention or an antibody of the invention and directly or indirectly detecting binding of prefibrillar oligomers or prefibrillar oligomers or protofibrils present in such tissue or fluid as an indication of the presence or likelihood of disease. In one embodiment, the tissue or fluid is cerebrospinal fluid. The disease characterized by amyloid deposits may comprise, without limitation, one or more of the following: Alzheimer's, early onset Alzheimer's associated with Down's syndrome, SAA amyloidosis, hereditary Icelandic syndrome, multiple myeloma, and spongiform encephalopathies, including mad cow disease, sheep scrapie, and mink spongiform encephalopathy, Parkinson's disease, Huntington's disease, amyotropic lateral sclerosis, Creutzfeld Jakob disease, Gerstmann-Straussler-Scheinker syndrome, kuru, fatal familial insomnia, chronic wasting syndrome, transthyretin-related amyloidosis, for example, familial amyloid polyneuropathy and serum amyloidosis, frontotemporal dementia, type II diabetes, systemic amyloidosis, British familial dementia, Danish familial dementia, macular degeneration, glaucoma, and cerebrovascular amyloidosis. The amounts of antibody may be measured as antibody titers. In one embodiment, amounts of antibody are measured using an ELISA assay.

Still further in accordance with the invention, there are provided methods of assessing efficacy of a treatment method of a human or animal having a disease characterized by amyloid deposits which includes, for example, determining a baseline amount of an antibody specific for an antigen comprising a composition of the invention in a first tissue or fluid sample from a patient taken before treatment with an agent, and comparing an amount of the antibody in a second tissue or fluid sample from the subject taken after treatment with the agent to the baseline amount of the antibody. In one embodiment, a reduction or lack of significant difference between the amount of the antibody measured after the treatment compared to the baseline amount of the antibody indicates a negative treatment outcome. In another embodiment, a significantly greater amount of the antibody measured after the treatment compared to the baseline amount of the antibody indicates a positive treatment outcome.

Still further in accordance with the invention, there are provided methods of assessing efficacy of a treatment method of a human or animal having a disease characterized by amyloid deposits which may include determining a baseline amount in tissue sample from a patient before treatment with an agent of a oligomer or prefibrillar oligomer prefibrillar oligomer or protofibrillar aggregate selectively or specifically binding an antibody produced using the epitope-containing composition of the present invention, and comparing an amount of the oligomer or prefibrillar oligomer prefibrillar oligomer or protofibrillar aggregate determined using the same antibody preparation after treatment with the agent to the baseline amount of the oligomer prefibrillar oligomer or protofibrillar aggregate. In one embodiment, a reduction or lack of significant difference between the amount of the oligomer or prefibrillar oligomer prefibrillar oligomer or protofibrillar aggregate measured after the treatment compared to the baseline amount of the oligomer prefibrillar oligomer prefibrillar oligomer or protofibrillar aggregate indicates a negative treatment outcome. In another embodiment, a significantly greater amount of the oligomer prefibrillar oligomer prefibrillar oligomer or protofibrillar aggregate measured after the treatment compared to the baseline amount of the oligomer prefibrillar oligomer prefibrillar oligomer or protofibrillar aggregate indicates a positive treatment outcome.

Still further in accordance with the invention there are provided methods of making the compositions of the present invention, comprising producing a peptide comprising at least 6 (preferably at least 8, or at least 9) random amino acids which will form a β-sheet structure when the monomers are joined to a surface allowing for the formation of self assembled peptide monolayers.

Still further in accordance with the invention there are provided methods of making the compositions of the present invention, comprising producing a peptide comprising at least 6 (preferably at least 8, or at least 9) random amino acids which are covalently coupled to a surface allowing for the formation of self assembled peptide monolayers.

Still further in accordance with the invention there are provided methods of making the compositions of the present invention, comprising producing a peptide comprising at least 6 (preferably at least 8, or at least 9) random amino acids which are covalently coupled to a surface selected from the group consisting of gold, zinc, cadmium, tin, titanium, silver, selenium, gallium, indium, arsenic, silicon, mixtures thereof or combinations thereof.

Still further in accordance with the invention, there are provided methods of monitoring amyloid disease or susceptibility thereto in a human or animal comprising detecting an immune response against a epitope-containing composition of the invention in a sample from the patient.

Still further in accordance with the invention, the amounts of antibody produced using the epitope-containing composition of the present invention may be measured as antibody titers and the amounts of antigen may be measured as antigen titers. In one embodiment, the amounts of antibody are measured by an ELISA assay. In one embodiment, the amounts of antigen are measured by an ELISA assay.

Still further in accordance with the invention, the detecting of an immune response may include detecting the presence or absence of an antibody that selectively or specifically binds to a composition of the invention and/or detecting the presence or absence of T-cells selectively or specifically reactive with a composition of the invention.

Still further in accordance with the invention, there are provided diagnostic kits useful for detecting a disease characterized by the presence of amyloid deposits, which diagnostic kits may include an isolated composition of the invention which includes an antigen of the invention.

Each and every feature described herein, and each and every combination of two or more of such features, is included within the scope of the present invention provided that the features included in such a combination are not mutually inconsistent.

These and other aspects and advantages of the present invention are set forth in the following figures, detailed description, examples and claims.

DEFINITIONS

Figure 1:
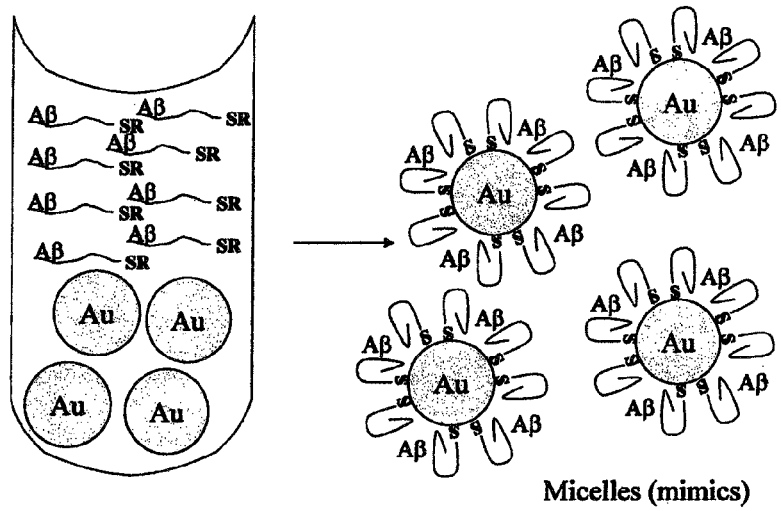
FIG. 1 shows a schematic diagram of the assembly of a synthetic conformationally constrained random peptide antigen of the invention. The 3A peptide replaces the Aβ peptide shown in the diagram. The peptide is covalently coupled to the colloidal gold via a carboxy terminal thiol.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

The term "A" or "Aβ peptide" refers to peptides which comprise low molecular weight soluble oligomers, oligomer prefibrillar oligomer prefibrillar oligomer or protofibrillar aggregates, fibrils and amyloid deposits each associated with AD. Amyloid Aβ peptides include, without limitation, Aβ 39, Aβ 40, Aβ 41 Aβ 42 and Aβ 43 which are 39, 40, 41, 42 and 43 amino acid amino acids in length, respectively.

The term "amyloid" refers to insoluble protein aggregates sharing a cross-β quaternary structure, due to misfolding of unstable peptides or proteins. A cross-β structure comprises β-strands (generally a stretch of 6-15 amino acids whose peptide backbone is more or less fully extended) of multiple peptides contributing by hydrogen bonding to a multimeric β-sheet structure. Many, but not all, amyloids exhibit apple-green birefringence when stained with Congo red and viewed under polarized light.

As used herein, the terms "peptide" and "protein" are intended to include peptides comprised of naturally-occurring L-amino acids, as well as peptide derivatives, peptide analogues and peptide mimetics of the naturally-occurring L-amino acid structures. The term "amino acid" should, unless otherwise indicated as being unmodified, be interpreted to mean a naturally occurring, modified or derivatized amino acid. Molecules comprising one or more modified or derivatized amino acid may include molecules which mimic the chemical structure of a peptide, such as the peptide linkage, and retain the functional properties of a peptide. Approaches to designing peptide analogues, derivatives and mimetics are known in the art. For example, see Farmer, P. S. in *Drug Design* (E. J. Ariens, ed.) Academic Press, New York, 1980, vol. 10, pp. 119-143; Ball. J. B. and Alewood, P. F. (1990) *J. Mol. Recognition* 3:55; Morgan, B. A. and Gainor, J. A. (1989) *Ann. Rep. Med. Chem.* 24:243; and Freidinger, R. M. (1989) *Trends Pharmacol. Sci.* 10:270.

The term "amyloid peptide" refers to a peptide that is present in amyloid forms including amyloid peptide intermediates, low molecular weight soluble oligomers, prefibrillar soluble oligomers, protofibrils, annular protofibrils, soluble amyloid fibrils, insoluble amyloid fibrils and amyloid plaques.

The term "antibody" includes intact antibodies, naturally occurring or synthetic, binding fragments, and derivatives (including humanized and/or veneered versions) thereof, including but not limited to, for example, full-length antibodies (e.g., an IgG antibody) or only an antigen binding portion (e.g., a Fab, F(ab')$_2$ or scFv fragment). Typically, fragments compete with the intact antibody from which they were derived for specific binding to an antigen. Optionally, antibodies or binding fragments thereof, can be chemically conjugated to, or expressed as, fusion proteins with other proteins, or may comprise antibody mimics such as those synthetic binding molecules derived from fibronectin, such as such molecules termed ADNECTINS®.

"Anti-oligomer antibody" or "Anti-oligomer" refer to an antibody that binds to prefibrillar oligomers or amyloid peptide aggregate intermediates but does not bind to or does not specifically bind to amyloid peptide monomers, or amyloid peptide fibrils.

Compositions or methods "comprising" one or more recited elements may include other elements not specifically recited. For example, a composition that comprises an amyloid Aβ peptide may encompass both an isolated amyloid Aβ peptide as a component of a larger polypeptide sequence or as part of a composition which includes multiple elements.

The term "epitope" or "antigenic determinant" refers to a site on an antigen to which B and/or T cells respond or a site on a molecule against which an antibody will be produced and/or to which an antibody will bind. For example, an epitope can be recognized by an antibody defining the epitope.

A "linear epitope" is an epitope wherein an amino acid primary sequence comprises the epitope recognized. A linear epitope typically includes at least 3, and more usually, at least 5, for example, about 8 to about 10 amino acids in a unique sequence.

A "conformational epitope", in contrast to a linear epitope, is an epitope wherein the primary sequence of the amino acids comprising the epitope is not the sole defining component of the epitope recognized (e.g., an epitope wherein the primary sequence of amino acids is not necessarily recognized by the antibody defining the epitope). Typically a conformational epitope comprises an increased number of amino acids relative to a linear epitope. With regard to recognition of conformational epitopes, the antibody recognizes a 3-dimensional structure of the peptide or protein. For example, when a protein molecule folds to form a three dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography 2-dimensional nuclear magnetic resonance spectroscopy and site-directed spin labeling and electron paramagnetic resonance spectroscopy. See, for example, Epitope Mapping Protocols in *Methods in Molecular Biology*, Vol. 66, Glenn E. Morris, Ed. (1996), the disclosure of which is incorporated in its entirety herein by reference.

The term "immunological response" or "immune response" relates to the development of a beneficial humoral (antibody mediated) and/or a cellular (mediated by antigen-specific T cells or their secretion products) response directed against an amyloid peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4$^+$ T helper cells and/or CD8$^+$ cytotoxic T cells. The response may also involve activation of monocytes, macrophages, NK cells, basophils, dendritic cells, astrocytes, microglia cells, eosinophils or other components of innate immunity.

An "immunogenic agent" or "immunogen" or "antigen" is capable of inducing an immunological response against itself upon administration to a subject, optionally in conjunction with an adjuvant.

"Isolated" means purified, substantially purified or partially purified. Isolated can also mean present in an environment other than a naturally occurring environment. For example, an antibody that is not present in the whole blood serum in which the antibody would ordinarily be found when naturally occurring is an isolated antibody.

The term "patient" includes human and other animal subjects that receive therapeutic, preventative, diagnostic or experimental treatment or a human or animal having a disease or being predisposed to a disease.

"Oligomer or protofibrillar aggregates", "micellar aggregates", "prefibrillar oligomers," "high molecular weight amyloid peptide aggregates", "high molecular weight soluble amyloid peptide aggregates" "amyloid peptide aggregates", "soluble aggregate intermediates", "amyloid oligomeric intermediates", "oligomeric intermediates" and "oligomeric aggregates" or simply, "intermediates" refer to aggregations which include more than two or more individual peptide or protein monomers. The upper size of oligomer prefibrillar oligomer prefibrillar oligomer or protofibrillar aggregates includes aggregations of oligomers which form spherical structures or micelles and stings of micelles which lead to fibril formation.

"Annular protofibrils" are a particular subset of oligomer prefibrillar oligomer prefibrillar oligomer or protofibrillar aggregates in which 3 to 10 spherical oligomer subunits are arranged in an annular or circular fashion with a hollow center that appears as a pore in electron or atomic force micrographs.

The molecular weight of a oligomer prefibrillar oligomer prefibrillar oligomer or protofibrillar aggregate may be in a range of about 10 kDa to about 100,000,000 KDa, for example, about 10 kDa to about 10,000,000 or 1,000,000 KDa. However, this size range is not intended to be limiting and oligomer prefibrillar oligomer prefibrillar oligomer or protofibrillar aggregates are not defined by a molecular weight range.

"Protofibrils" are oligomer prefibrillar oligomer prefibrillar oligomer or protofibrillar aggregates which include spherical structures comprising amyloid Aβ peptides that appear to represent strings of the spherical structures forming curvilinear structures.

As used herein, the term "therapeutics" is to be interpreted to include vaccines capable of initiating an immune response against amyloid prefibrillar oligomers such that the aggregates are neutralized before they are able to exert the cytotoxic effects that they otherwise would (or could) in the absence of such vaccine. Therapeutics such as these may be used to elicit a short term immune response in the event of acute sequelae of disease, or a longer term immune response as a prophylatic to prevent amyloid-related disease, or to prevent or lessen the progression of such disease.

As used herein, the term "selective" means that the binding constant governing the binding between the components of a binding pair, such as a given antibody, or set of antibodies, produced to bind a given antigen, or set of antigens, is at least 10-fold, (or at least 50 fold, or at least 100-fold, or at least $10^3$-fold, or at least $10^5$-fold or at least $10^6$-fold) higher than the binding constant between either component and any other antibody or antigen present in the sample being tested.

As used herein, the term "specific binding" means that the binding between the components of a binding pair, such as a given antibody, or set of antibodies, produced to bind a given antigen, or set of antigens, is detectable under test conditions, whereas the binding between either component and any other antibody or antigen present in the sample being tested is not statistically significant using the same test conditions. Affinities greater than $10^6$ $M^{-1}$, or $10^7$ $M^{-1}$, or $10^8$ $M^{-1}$, or $10^9$ $M^{-1}$, or $10^{10}$ $M^{-1}$ are preferred for specific binding.

The term "substantial identity" means that two peptide sequences, when optimally aligned, such as by the programs GAP or BESTFIT using default gap weights, share at least 65 percent sequence identity, for example, at least 80 percent or 90 percent sequence identity, or at least 95 percent sequence identity or more, for example, 99 percent sequence identity or higher.

Preferably, amino acid residue positions in an alignment which are not identical differ by conservative amino acid substitutions, i.e., substitution of an amino acid for another amino acid of the same class or group. Some amino acids may be grouped as follows: Group I (hydrophobic side chains): leu, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Non-conservative substitutions may include exchanging a member of one of these classes for a member of another class.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm may then be used to calculate the percent sequence identity for the test sequence (s) relative to the reference sequence, based on the designated program parameters. Optimal alignment of sequences for comparison can be conducted, for example, by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available and accessible at no cost through the National Center for Biotechnology Information. Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix, see for example, Henikoff & Henikoff, Proc. Natl. Acad. Sci. USA 89,10915 (1989). Conservative substitutions involve substitutions between amino acids in the same class.

"Synthetic" means not naturally occurring. For example, a synthetic composition is a composition that is not found occurring in nature.

A "therapeutic agent" or "therapeutic" is a substance useful for the treatment or prevention of a disease in a patient. Therapeutic agents of the invention are typically substantially pure. This means that an agent is typically at least about 50% w/w (weight/weight) pure, as well as being substantially free from proteins and contaminants which interfere with the efficacy of the therapeutic. The agents may be at least about 80% w/w and, more preferably at least 90% w/w or about 95% w/w in purity. However, using conventional protein purification techniques, homogeneous peptides of 99% w/w or more can be produced. A therapeutic agent may be a component of a composition at any therapeutically effective concentration.

DETAILED DESCRIPTION OF THE INVENTION

The present invention provides for compositions having one or more epitopes antigentically, but not necessarily physically, substantially identical or identical to epitopes that are found on amyloid peptide aggregates which are present in humans or animals having a disease characterized by amyloid deposits, antibodies to such epitopes and methods for making and using the compositions and antibodies.

More particularly, the invention includes, without limitation, compositions comprising an epitope, for example, a conformational epitope comprised of peptide monomers having a β strand conformation that, when used to immunize a mammal result in the formation of antibodies that selectively or specifically bind epitopes found on a peptide aggregate, for example, an amyloid peptide aggregate in a human or animal having a disease characterized by amyloid deposits. In particular, the invention includes conformational epitopes comprised of peptides of random amino acid sequence that are antigenically similar, or identical to the epitopes found on a peptide aggregate. Preferably the peptides are from 6-20 amino acids in length, more preferably from 8 to 12 amino acids in length, even more preferably the peptides are 8, or 9, or 10, or 11 or 12 or 13 or 14 or 20 amino acids in length. Even more preferably, the peptides are joined to a surface capable of conformationally constraining the tertiary and/or quaternary structure of the peptides.

The invention also includes methods of making the epitope-containing compositions, such as by choosing amino acids from a pool of available amino acids having a high probability of forming a β sheet tertiary or quaternary structure, to make a population of peptides comprising the chosen amino acids that are antigenically similar or identical, when their conformation is constrained, such as by being joined to an appropriate surface, to the epitopes found on a peptide aggregate. In certain aspects the random peptides may comprise alternating polar and non-polar residues. The peptides can be synthesized using standard peptide synthesis procedures, such as solid phase protein synthesis (SPPS) techniques as described in e.g., Atherton, E., Sheppard, R. C., *Solid Phase Peptide Synthesis: A Practical Approach*, IRL Press, Oxford, England, 1989 and Stewart J. M., Young, J. D. *Solid Phase Peptide Synthesis*, (2nd ed., Pierce Chemical Company, Rockford, 1984). Such methods may include synthesizing or derivatizing the antigenic peptides of the present invention with an active group or moiety capable of covalently or noncovalently joining (for example, binding, adsorbing, and/or chelating) the peptide to a surface. In a preferred embodiment the peptides are synthesized as a thioester for adsorption to a suitable active surface, such as gold colloidal particles.

The present invention also includes methods of using the compositions including, without limitation, for the detection, treatment and prevention of diseases, antibodies against the conformational epitopes present in the compositions, methods of immunizing a mammal against prefibrillar oligomers, methods of making selective or specific antibodies to prefibrillar oligomers, and methods of using the antibodies including, without limitation, for the detection, treatment and prevention of diseases.

Amyloid diseases are characterized by the accumulation of amyloid plaques or precursors to amyloid plaques in patients or the predisposition to the accumulation of amyloid plaques or precursors to amyloid plaques in patients. One of the primary constituents of amyloid plaques are amyloid peptides. The general conformation of amyloid peptides may vary from disease to disease, but often the peptide has a characteristic β-pleated sheet structure. Amyloid peptides and amyloid-like peptides include peptides and proteins of about 8, or about 9, or about 10, or about 11, or about 12, or about 13, or about 14, or about 15, or about 20 amino acids to about 200 amino acids in length. However, this size range is not intended as a limitation on the size of the epitopes of the present invention, and amyloid or amyloid-like peptides or proteins having fewer or more amino acids are contemplated in the present invention.

Oligomer or protofibrillar aggregates are intermediates in the production of insoluble fibrils that accumulate in amyloid plaques of humans or animals having a disease characterized by amyloid deposits, for example, Alzheimer's disease. oligomer prefibrillar oligomer prefibrillar oligomer or protofibrillar aggregates include aggregates which may be as small as four amyloid peptides, as small as five amyloid peptides, as small as six amyloid peptides, as small as seven amyloid peptides or as small as eight amyloid peptides. In one embodiment, oligomer or prefibrillar oligomers are micellar aggregates or micelles or strings of micelles. oligomer prefibrillar oligomer or protofibrillar aggregates are effective to form a conformational epitope which is recognized by an antibody of the present invention.

The conformational epitopes of the present invention which are antigenically substantially similar or identical to those found on oligomer prefibrillar oligomer or protofibrillar aggregates are substantially not found in the native precursor proteins for amyloid peptides, for example, amyloid peptide monomers, dimers, trimers or tetramers, nor in the mature amyloid fibers that are defined by their characteristic cross β-sheet x-ray fiber diffraction pattern or in amyloid plaques. The oligomer prefibrillar oligomer or protofibrillar aggregates that are substantially antigenically similar or identical to the epitopes of the present invention contain the specific polypeptide structure which results in conformational epitopes that are recognized by antibodies of the present invention have a size range of approximately a dimer, trimer, tetramer, pentamer, a hexamer, a heptamer or an octamer to micellar forms or protofibrils which have a molecular weight in excess of 1,000,000 Daltons.

Immunogens of the present invention include compositions comprising peptides having a substantially random primary amino acid sequence comprised of amino acids tending to form a β-sheet tertiary or quaternary amino acid sequence. These peptides are preferably conformationally constrained, for example, by being joined to a surface. Without intending to be limited to any particular surface, preferably such surface is a colloidal surface, such as colloidal gold. Antibodies of the invention are effective to selectively or specifically bind to these immunogens.

Immunogens of the present invention may be obtained from any suitable source. For example, the immunogens may be purified from naturally occurring sources or may comprise purified fragments of naturally occurring peptides. In one particularly useful embodiment, the immunogens are synthetic.

Peptides useful in the present invention may be obtained from natural sources, for example, purified from a naturally occurring source, or they may be manufactured. Methods of manufacture include any suitable method including, but not limited to, solid phase synthesis and heterologous gene expression.

The fact that the present antigen is common to amyloids of widely varying primary sequence Indicates that the epitope is formed from a specific three dimensional conformation of the polypeptide backbone or the surface of the beta sheets referred to as a conformational epitope Solid phase synthesis and purification of peptides may be carried out by fluoren-9-ylmethoxy carbonyl chemistry using a continuous flow semiautomatic instrument as is described in D. Burdick et al. (1992) *J Biol Chem* 267, 546-54 the disclosure of which is incorporated herein by reference.

The first Fmoc-amino acid is manually coupled to sulfamylbutyry-AM-PEGA resin (Novabiochem, San Diego, Calif.) in Dichloro methane (DCM). To this is added diisopropylethylamine (DIEA); the mixture is stirred for 20 min. at room temperature, cooled to −10 to −20° C. and ByBop (benzotriazol-1-yl-oxy-tris(pyrrolidino)-phosphonium hexafluorophosphate) is added. The mixture is stirred for 8 to 9 hours at −10 to −20° C. The coupling efficiency may be checked using the Kaiser test, which is well known in the art of peptide synthesis.

Acetylation may be performed using acetic anhydride. Amino acid chain elongation is by fluoren-9-ylmethoxy carbonyl chemistry using a continuous flow semiautomatic instrument. The peptide is washed with 5×N-methyl-2-pyrrolidone (NMP), 5.0 mL of NMP, 185 μL of i-Pr2EtN (1.1 mmol), and 400 μL of iodoacetonitrile (previously filtered through an alumina basic filter bed in the dark) in a synthesis vessel. The reaction mixture is then shaken for 24 h in the dark on a rotary plate. The resin is washed with 5×NMP and 5×DMF followed by a wash using 5×$CH_2Cl_2$ and then dried. Resin is washed with 5×THF followed by the addition of THF and TMS-$CH_2N_2$ (50:50, v/v, hexane). After stirring for 2 h, the resin is washed with THF and DMF.

The resin is added to 120 μL of ethyl-3mercaptopropionate and the mixture shaken on a rotary plate for 24 h. The resin is filtered then washed with 3×3 ml DMF. The filtrate and washes are collected and rotary evaporated at 34° C.

The resulting peptides are deprotected using standard methods (TFA and scavengers), and purified by RP-HPLC. The purity may be checked by analytical RP-HPLC and electrospray mass spectrometry.

The peptides may also be produced by standard heterologous gene expression methods. For example, recombinant expression can be in bacteria, such as *E. coli*, or in yeast, insect cells or mammalian cells. Procedures for recombinant protein expression are described by Sambrook et al., *Molecular Cloning: A Laboratory Manual* (C. S. H. P. Press, NY 2d ed., 1989). In addition, many amyloid peptides including human insulin or lysozyme may be obtained from commercial sources.

The peptides useful in the present invention may be advantageously aggregated or conformationally constrained to form an epitope useful as described herein. In one useful embodiment, the peptides are associated with a surface for example, physically joined (attached, adsorbed or chemically bonded) in such a manner so as to allow for the production of an epitope which is recognized by antibodies selectively or specifically indicating the presence of prefibrillar oligomers.

For example, a C-terminal thioester may be attached to the peptides in a conventional manner as is known to those of ordinary skill in the field. For example, C-terminal thioesterification of the peptides by Fmoc chemistry may carried out essentially as described in Inginito, R. et al., (1999) *Journal of the American Chemical Society* 121, 11369-11374. C-terminal thioesterified peptides will readily attach to a surface such as a gold metallic surface.

The surface to which the peptides are associated with or attached to may be any suitable surface. For example the surface may be solid. The surface may include one or more of hydrocarbons, a polymer or polymers, plastic, glass, metal, ceramic or one or more biomolecules such as proteins, fats, nucleic acids and carbohydrates. More than one of these components may comprise the surface. For example, a particle may comprise a polymer coated with a metal. The surface may be flat or have a three dimensional shape such as a curved surface. In addition, the surface may be a particle. In one embodiment, oligomeric aggregate molecular mimics are produced using nanospheres. The nanospheres may be of any suitable size. For example, the diameter of the nanospheres may be in a range of about 0.01 nm to about 1 cm. In one useful embodiment, the nanospheres are about 5 nm in diameter.

In one particular embodiment, gold nanospheres are used to produce molecular mimics. Briefly, the nanospheres may be incubated in a solution of 0.2 mg/ml of the C-terminal thioester peptide, pH (5.0-5.5) for 3 h followed by pH adjustment to 7.4 with 100 mM Tris pH 8.0 (0.2% sodium azide). After incubation for 6 h at room temperature, the molecular mimics are collected by centrifugation and washed three times with PBS pH 7.6 to remove unincorporated peptide and are then stored in 0.02% sodium azide at 4° C. Assembly of such a molecular mimic is shown in FIG. 1. This is but an example of a method for producing molecular mimics and epitopes of the invention. Other methods of producing the epitopes will be readily apparent to those of ordinary skill in the art.

The invention includes antibodies that recognize an epitope present in a composition of the present invention, and on amyloid intermediates, but do not recognize epitopes present on amyloid monomers, or epitopes of mature amyloid fibrils or those of amyloid deposits which comprise amyloid peptides aggregated in an insoluble mass.

Antibodies of the present invention may be made by any suitable means. For example, the antibodies may be produced in laboratory animals. In one such case, New Zealand white rabbits, Balb/C, C57/Black6 mice or domestic dogs are injected with a quantity of molecular mimic produced as described above. The antigen is mixed with incomplete Freund's adjuvant, alum adjuvant or with no adjuvant (PBS only) prior to injection. For the first injection, equal parts antigen and adjuvant are used. For subsequent injections, the antigen is mixed with adjuvant and each injected, for example, at 2-week intervals. Animals may be injected subcutaneously in small increments of 0.1 mL per site in a checkerboard fashion on the scapular region.

The antigenic peptides of the present invention are constrained in a conformation that results in the production and display on the solvent accessible surface of the conformation-dependent prefibrillar oligomer epitope that is recognized by the antibody. Specifically, the attachment of the carboxyl terminus to the surface substrate maintains this region in close apposition to the surface, an arrangement that mimics the arrangement of the Aβ peptide in soluble oligomers or prefibrillar oligomers or protofibrils. The attachment of the carboxyl terminus to the solid support prevents the rearrangement of this region of the peptide that occurs during the structural transition of soluble oligomers to amyloid fibrils. In amyloid fibrils, the carboxyl terminus is freely mobile and found at the solvent accessible surface of the amyloid fibril. The attachment of the carboxyl terminus to the solid support also maintains a parallel alignment of the polypeptide chains and prevents the dissociation of the polypeptide into its monomeric forms.

Very preferably the antigenic peptides of the present invention bind antibodies which will selectively or specifically bind oligomeric or protofibrillar aggregates. Also, the antigenic peptides very preferably comprise a primary amino acid sequence having no significant antigenic homology to a human protein. For example, a peptide epitope is at least 6-8 amino acids in length, see Paul, et al., *Fundamental Immunology* (3d ed., Raven Press, 1993) hereby incorporated by reference herein in its entirety. Thus, the antigenic peptides of the present invention have less than 8, or less than 7, or less than 6, or less than 5, or less than 4, or less than 3 continuous amino acids in common with a human protein. Preferably, the antigenic peptides of the present invention have no more than 4 contiguous amino acids in common with a human protein. Lack of homology to human peptides or proteins can be determined using a BLAST search of a candidate peptide against a database containing human protein sequences, for example, the NCBI's GenBank and RefSeq databases available via the internet at http://www.ncbi.nlm.nih.gov/

Certain presently preferred antibodies that bind to the antigenic peptides of the present invention remain bound during wash times of more than one hour and, thus, appear to exhibit relatively high binding affinity. In at least some of the antibodies of the present invention, the half time for dissociation is greater than one hour.

The present Applicants have discovered that such antibodies recognize an epitope that is shared or common to soluble oligomers or prefibrillar oligomers or protofibrils from a broad range of amyloidogenic peptides and proteins regardless of sequence. This epitope is absent or substantially reduced in its structure or accessibility in the low MW forms of the peptides and in the amyloid fibrils. The epitope consists of common structural and conformational features of the peptide, including but not limited to a specific conformation of the polypeptide backbone that is formed by many different protein and peptide sequences. The epitope recognized by the antibody is such that the binding of an antibody to the epitope substantially reduces or eliminates the toxicity of the soluble oligomers regardless of the protein or peptide sequence that display the epitope. It is to be understood, however, that this description of the inventions does not necessarily exclude antibodies that are selective or specific for different sequences and which do not recognize all the other amyloids.

For serum collection the IgG fraction (or if monoclonal antibodies are to be purified from hybridoma clone lysates, cell lysates), may be affinity purified, for example, on Protein G-Sepharose beads, eluted, then dialyzed against PBS. The intermediate aggregate-selective or -specific antibodies may be purified by adsorption on the constrained prefibrillar oligomer-selective or -specific peptides ("molecular mimics") produced as described above by mixing the molecular mimics with the IgG fraction and incubating for about 2 h, followed by washing. After elution, the antibody may be dialyzed against PBS stored in PBS containing 0.02% sodium azide at 4° C. or at −70° C.

Polyclonal serum produced by vaccination of rabbits, dogs or other animals, or monoclonal antibody preparations isolated from hybridoma lysates made from with the molecular mimics disclosed herein is selective or specific for constrained prefibrillar oligomers and is not detectably reactive with soluble low molecular weight or fibrillar amyloid species. Surprisingly, no significant anti-oligomer immunoreactivity against low molecular weight aggregates or fibrils is observed for the unfractionated serum indicating that the immune response to the molecular mimics is very selective specific. For example, antibodies produced against constrained antigenic peptides of the present invention will bind Aβ prefibrillar oligomers but do not substantially bind to Aβ low molecular weight aggregates or to Aβ fibrils.

Antibodies produced against Aβ peptide aggregate mimics (as well as against random B-sheet peptides) are shown to bind to amyloid prefibrillar oligomers of all other amyloid types examined. In addition, these antibodies are shown to neutralize the toxicity of oligomeric forms of all toxic amyloids (i.e., amyloid oligomer prefibrillar oligomer or protofibrillar aggregates) examined. The implication is that amyloid oligomers or prefibrillar oligomers share a common structure. Therefore, the present invention contemplates that antibodies produced using a molecular mimic which is constrained to assume such a structure will produce an antibody (e.g., a conformation dependent antibody) selective or specific for other amyloid peptide oligomers or protofibrillar aggregates types, for example, all amyloid peptide prefibrillar oligomers types. For example, it is contemplated that antibodies prepared from molecular mimics comprising constrained peptides having a random amino acid sequence and a β-sheet conformation will selectively or specifically react with oligomer or prefibrillar oligomer or protofibrillar aggregates of Aβ peptide, insulin, synuclein, and other amyloid prefibrillar oligomers, for example, all other amyloid prefibrillar oligomer forms.

Each of the following antigenic peptides of random primary amino acid sequence have been shown to form amyloid prefibrillar oligomers which produce a conformational epitope recognized by antibodies selective or specific against amyloid peptides. Some of these latter peptides are present in amyloid deposits of humans or animals having a disease characterized by the amyloid deposits. The present invention is not limited to the listed peptide or protein sequences or the specific diseases associated with some of the sequences. The present invention contemplates antibodies as described herein binding to at least one other amyloid peptide aggregate form or all other amyloid peptide aggregates. In particular, the present invention contemplates the application of methods and compositions of the present invention to other peptide or protein sequences which form amyloid precursor aggregates associated with other diseases.

Selected Amyloid Peptide Sequences

All of the amino acid sequences shown in this specification are written from the amino to carboxy terminal direction unless otherwise indicated.

```
Aβ40
                                            (SEQ ID NO 1)
DAEFRHDSGYEVHHQKLVFF AEDVGSNKGA IIGLMVGGVV

Aβ42
                                            (SEQ ID NO 2)
DAEFRHDSGY EVHHQKLVFF AEDVGSNKGA IIGLMVGGVV IA

Human Islet Amyloid Polypeptide (IAPP)
                                            (SEQ ID NO 3)
KCNTATCATQ RLANFLVHSS NNFGAILSST NVGSNTY Human Prion 106-126
                                            (SEQ ID NO 4)
KTNMKHMAGA AAAGAVVGGL G
```

Stefani and coworkers (Bucciantini et al (2002) *Nature* 416, 507-511) have recently reported that amyloid peptide aggregates formed from non-disease-related proteins are inherently cytotoxic, suggesting that they may have a structure in common with disease related amyloid peptides. Non-disease related amyloid peptide aggregates comprising the following non-disease related amyloid peptides also bind the antibodies of the present invention.

```
Poly glutamine synthetic peptide KK(Q40)KK
                                            (SEQ ID NO 5)
KKQQQQQQQQ QQQQQQQQQQ QQQQQQQQQQ QQQQQQQQQQ
QQKK Human Lysozyme
                                            (SEQ ID NO 6)
MKALIVLGLV LLSVTVQGKV FERCELARTL KRLGMDGYRG
SLANWMCLA KWESGYNTRA TNYNAGDRST DYGIFQINSR
```

```
-continued
YWCNDGKTPG AVNACHLSC SALLQDNIAD AVACAKRVVR
DPQGIRAWVA WRNRCQNRDV RQYVQGCGV Human Insulin
                                         (SEQ ID NO 7)
MALWMRLLPL LALLALWGPD PAAAFVNQHL CGSHLVEALY
LVCGERGFFY TPKTRREAED LQVGQVELGG GPGAGSLQPL
ALEGSLQKRG IVEQCCTSIC SLYQLENYCN Human Transthyretin
                                         (SEQ ID NO 8)
MASHRLLLLC LAGLVFVSEA GPTGTGESKC PLMVKVLDAV
RGSPAINVAV HVFRKAADDT WEPFASGKTS ESGELHGLTT
EEEFVEGIYK VEIDTKSYWK ALGISPFHEH AEVVFTANDS
GPRRYTIAAL LSPYSYSTTA VVTNPKE Human Alpha Synuclein
                                         (SEQ ID NO 9)
MDVFMKGLSK AKEGVVAAAE KTKQGVAEAA GKTKEGVLYV
GSKTKEGVVH GVATVAEKTK EQVTNVGGAV VTGVTAVAQK
TVEGAGSIAA ATGFVKKDQL GKNEEGAPQE GILEDMPVDP
DNEAYEMPSE EGYQDYEPEA Random Peptide 2A
                                         (SEQ ID NO: 10)
FIYLIFVSSH LYSTSLLYHT Random Peptide 3A
                                         (SEQ ID NO: 11)
TYLIHVHIIT IYHISIYYIV Random Peptide 3B
                                         (SEQ ID NO: 12)
TFHVTVYLSL SFTFSLSFSV Random Peptide 4B
                                         (SEQ ID NO: 13)
TIYFYFYFYL TLHFYFTISI
```

In addition, prefibrillar oligomers formed from variants and fragments of wild type AB42, AB40 including, without limitation AB42 (A21 G) Flemish mutation), AB42 (E22Q) Dutch mutation, AB42 (E22G) Arctic mutation, AB42 (D23N) Iowa mutation, AB40 (A21G) Flemish mutation), AB40 (E22Q) Dutch mutation, AB40 (E22G) Arctic mutation, AB40 (D23N) Iowa mutation, AB40 (E22Q & D23N) Dutch & Iowa mutations, Aβ 3-42 (pGlu 3), Aβ 340 (pGlu 3), A8-42, A17-42, A1-16, A3-11, A25-35, A4-16 (3 analogues, $Cys^{16}$ A4-16, $Ala^4$ A4-16, and Ala, A4-16), His6 (SEQ ID NO: 14) AC40 (6 histidines (SEQ ID NO: 14) appended to the amino terminus of AC40) are recognized by the antibodies of the present invention. Other prefibrillar oligomers recognized by antibodies of the invention include, without limitation, prefibrillar oligomers formed from IAPP (C2A and C7A) where alanine is substituted for the naturally occurring cysteine in IAPP, polyglutamine KKQ40KK (SEQ ID NO: 5) or poly glutamine where the number of Q residues is greater than 32, Calcitonin, TTR and its mutants TTR $Pro^{55}$; TTR $Phe^{78}$, vitronectin, poly lysine, poly arginine, serum amyloid A, cystanin C, IgG kappa light chain, prefibrillar oligomers produced from other amyloid peptides disclosed herein and amyloid intermediates associated with amyloid diseases disclosed herein.

The present invention provides for amyloid disease therapeutics which induce a specific immune response against amyloid prefibrillar oligomers. These therapeutics include the peptide epitope molecular mimics described herein which comprise a peptide having a random primary sequence of β-sheet forming amino acids, preferably joined to a surface, that induce the production of and/or cross-react with antibodies selective or specific to at least one class of amyloid prefibrillar oligomers. Induction of an immune response can be a) active as when an immunogen is administered to induce an immune response, such as the production of antibodies or T-cells selectively or specifically reactive with amyloid prefibrillar oligomers in a patient, or b) passive, as when an antibody is administered to a mammal, such as a human, that itself selectively or specifically binds to amyloid prefibrillar oligomers in the patient.

The peptides and proteins of the present invention may in certain cases include unnatural amino adds or modifications of N or C terminal amino acids. Examples of unnatural amino acids are disubstituted amino acids, alkyl amino acids, lactic acid, 4-hydroxyproline, carboxyglutamate, e-N, N,N-trimethyllysine, e-N-acetyllysine, O-phospgoserine, N-acetylserine, N-formylmethionine, 3-methylhistidine, 5-hydroxylysine, and w-N-methylarginine. Other modified, derivatised, rare, D-, or non-naturally occurring amino acids are well known in the art.

When used as therapeutics the antigenic peptides of the present invention are preferably chosen to have an amino acid sequence distinct from that of a human protein or peptide to prevent an autoimmune reaction. Thus, the antigenic peptides of the present invention have less than 8, or less than 7, or less than 6, or less than 5, or less than 4, or less than 3 continuous amino acids in common with a human protein. Preferably the antigenic peptides of the present invention have no more than 4 contiguous amino acids in common with a human protein.

The compositions of the present invention may comprise a one or more carrier protein combined with or joined to the antigenic peptides of the present invention. For example, the composition may comprise a fusion protein comprising a carrier protein domain and an antigenic peptide domain. Alternatively, the carrier protein may be present in the composition of the present invention in a manner distinct from the antigenic peptides of the present invention.

Peptides constructed or synthesized as disclosed herein may be further analyzed for capacity to induce antibodies or reactive lymphocytes to oligomeric intermediates. For example, multiple dilutions of sera can be tested on microtiter plates that have been precoated with an antibody selective or specific for a prefibrillar oligomers and a standard ELISA can be performed to test for reactive antibodies. Prospective antigenic peptide compounds can then be tested for prophylactic and therapeutic efficacy, for example, in transgenic animals predisposed to an amyloidogenic disease, as is understood in the art. Such animals include, for example, mice bearing a 717 mutation of APP described by Games et al., supra, and mice bearing a Swedish mutation of APP such as described by McConlogue et al., U.S. Pat. No. 5,612,486 and Hsiao et al., (1996) Science 274, 99; Staufenbiel et al., Proc. Natl. Acad. Sci. USA (1997) 94, 13287-13292; Sturchler-Pierrat et al., Proc. Natl. Acad. Sci. USA 94, 13287-13292; Borchelt et al., Neuron (1997) 19, 939-945. The same screening approach can be used on other potential therapeutics including those described above.

Therapeutics of the invention also include antibodies that specifically bind both to the antigenic peptides of the present invention and to prefibrillar oligomers. Such antibodies can be monoclonal or polyclonal. In one useful embodiment, the antibodies bind to a conformational epitope. The production of non-human monoclonal antibodies, for example, murine or rat, can be accomplished by, for example, immunizing the animal with an composition comprising an prefibrillar oligomer-like antigenic peptide of the invention. Also contemplated within the invention are methods comprising immunizing the animal with a purified prefibrillar oligomer-like antigenic peptide.

Humanized forms of mouse antibodies of the invention can be generated by linking the CDR regions of non-human antibodies to human constant regions by recombinant DNA techniques. See Queen et al., Proc. Natl. Acad. Sci. USA 86, 10029-10033 (1989) and WO 90/07861 (incorporated by reference for all purposes). Thus, the present antibodies may comprise, without limitation, a polyclonal or monoclonal antibody, an antibody fragment, such as a monovalent fraction antigen-binding papain fragment (Fab) or a bivalent fraction antigen binding pepsin fragment (F'ab$_2$). The antibodies or antibody fragments may be naturally occurring or genetically engineered. For example, the term "antibodies" may include chimeric antibodies comprising human $L_C$ and $H_C$ regions and $L_V$ and $H_V$ regions from another species, for example, from mouse cells. Chimeric antibodies are useful in the design of antibody-based drugs, since the use of unaltered mouse antibodies induces the production of human anti-mouse immunoglobulins and resultant clearance and reduction of efficacy.

However, chimeric antibodies, while having reduced immunogenicity as compared to the rodent antibody, do not solve all the problems that exist in the use of antibodies as drugs. For example, to minimize allotypic variation in the constant regions a human consensus sequence can be used representing the most common allotype in the general population. A further refinement has been used, called complimentarily determining region (CVDR) grafting. In this method, only the three antigen biding sites (formed by the three CDRs of the heavy chain and the three CDRs of the light chain) are excised from the murine antibodies and the nucleic acid regions encoding these CDRs are inserted (or "grafted") into a nucleic acid coding sequence encoding the framework region of the human antibody.

Further refinements may comprise what has been termed "reshaping", "veneering" and "hyperchimerization". In reshaping, the non-human variable region is compared with the consensus sequence of the protein sequence subgroup to which it belongs, as is the human framework compared with a consensus of the framework sequence for the antibody family to which it belongs. This analysis can identify amino acid residues that may be the result of mutation during the affinity maturation process; these residues are called "idiosyncratic". By incorporating the amino acid residues more common in human than a non-human in these positions, immunogenicity problems resulting from the idiosyncratic residues can be minimized.

Humanization by hyperchimerization involves a comparison of the human and murine non-CDR variable region sequences and the one with the highest homology is selected as the acceptor framework. Again, idiosyncratic residues are replaced with more highly conserved human ones. Those non-CDR residues that may interact with the CDR residues are identified and inserted into the framework sequence.

Veneering involves determining the three dimensional conformation of a humanized rodent (or other mammalian) antibody and replacing the exposed surface amino acids with those commonly found in human antibodies. In the first step the most homologous human variable regions are selected and compared to the corresponding non-human variable regions. In the second step, the mouse framework residues differing from the human framework are replaced with the human residues; only those residues fully or partially exposed at the surface of the antibody are changed.

While the humanization of antibodies provides therapeutic advantages not available in the use of non-human-derived or chimeric antibodies alone, new classes of peptide agents have been engineered to bind strongly to a desired target thereby antagonizing the normal activity of the target.

For example, fibronectins and fibronectin-related molecules (hereinafter collectively referred to as "fibronectins"), are multi-domain glycoproteins found in a soluble form in plasma, and in an insoluble form in loose connective tissue and basement membranes. They contain multiple copies of 3 repeat regions (types I, II and III), which bind to a variety of substances including heparin, collagen, DNA, actin, fibrin and fibronectin receptors on cell surfaces. Fibronectins are involved in a number of important functions: e.g., wound healing; cell adhesion; blood coagulation; cell differentiation and migration; maintenance of the cellular cytoskeleton; and tumor metastasis. The role of fibronectin in cell differentiation is demonstrated by the marked reduction in the expression of its gene when neoplastic transformation occurs. Cell attachment has been found to be mediated by the binding of the tetrapeptide RGDS (SEQ ID NO: 15) to integrins on the cell surface although related sequences can also display cell adhesion activity.

Plasma fibronectin occurs as a dimer of 2 different subunits, linked together by 2 disulphide bonds near the C-terminus. The difference in the 2 chains occurs in the type III repeat region and is caused by alternative splicing of the mRNA from one gene. The fibronectin type III (FnIII) repeat region is an approximately 100 amino acid domain, different tandem repeats of which contain binding sites for DNA, heparin and the cell surface. The superfamily of sequences believed to contain FnIII repeats represents 45 different families, the majority of which are involved in cell surface binding in some manner, or are receptor protein tyrosine kinases, or cytokine receptors.

Because a common characteristic of fibronectins is that they are involved in intermolecular binding, and due to the common scaffolding structure of the fibronectin molecule, such molecules are very useful templates for making and producing selective binding molecules capable of acting as antibody mimics. Such antibody mimics will often provide interference in preventing the interaction of the target "antigen" molecule or moiety with a binding partner, such as a selective or specific receptor. Thus, such selectively binding fibronectin molecules comprise ideal templates for making, for example, receptor antagonists. The FnIII loops comprise regions that may be subjected to random mutation and directed evolutionary schemes of iterative rounds of target binding, selection, and further mutation in order to develop useful therapeutic tools. Fibronectin based "addressable" therapeutic binding molecules (hereinafter "FATBIMs") may be useful. FATBIMs include the species of fibronectin-based binding molecules termed ADNECTINST™ by Compound Therapeutics, Inc.

Human antibodies may be obtained using phage-display methods. See, for example, Dower et al., WO 91/17271 and McCafferty et al., WO 92/01047. In these methods, libraries of phage are produced in which members display different antibodies on their outer surfaces. Phage displaying antibodies with a desired specificity are selected by affinity enrichment. Human antibodies against prefibrillar oligomers may also be produced from non-human transgenic mammals having transgenes encoding at least a segment of the human immunoglobulin locus and an inactivated endogenous immunoglobulin locus. See, for example, Lonberg et al., WO93/12227 (1993); Kucherlapati, WO 91/10741 (1991) (each of which is incorporated by reference in its entirety for all purposes). Human antibodies can be selected by competitive binding experiments, or otherwise, to have the same epitope specificity as a particular mouse or rabbit antibody.

Such antibodies are particularly likely to share the useful functional properties of the rodent antibodies.

Human polyclonal antibodies can also be provided in the form of serum from humans immunized with an immunogen of the invention. Optionally, such polyclonal antibodies can be concentrated by affinity purification using, for example, an immunogen of the invention as an affinity reagent.

Human or humanized antibodies can be designed to have IgG, IgD, IgA and IgE constant region, and any isotype, including IgG1, IgG2, IgG3 and IgG4. Antibodies can be expressed as a tetramer containing two light and two heavy chains, as separate heavy chains, light chains, as Fab, Fab' F(ab')$_2$ and Fv, or as single chain antibodies in which heavy and light chain variable domains are linked through a spacer.

Therapeutics for use in the present methods may also include T-cells that have been conditioned, through exposure to the prefibrillar oligomer-like antigenic peptides of the present invention to bind to amyloid prefibrillar oligomers. For example, T-cells may be activated against these amyloid intermediates by expressing a human MHC class I gene and a human-2-microglobulin gene from an insect cell line, whereby an empty complex is formed on the surface of the cells that can bind to a prefibrillar oligomers. T-cells contacted with the cell line may become specifically activated against the antigen. See e.g., Peterson et al., U.S. Pat. No. 5,314,813. Insect cell lines expressing an MHC class II antigen can similarly be used to activate CD4 T cells.

In certain instances it may be desirable to link an immunogen of the invention to a suitable carrier. Suitable carriers include serum albumins, keyhole limpet hemocyanin, immunoglobulin molecules, thyroglobulin, ovalbumin, tetanus toxoid, or a toxoid from other pathogenic bacteria, such as diphtheria, E. coli, cholera, or H. pylori, or an attenuated toxin derivative. Other carriers for stimulating or enhancing an immune response include cytokines such as IL-1, a mixture of IL-1 and β peptides, IL-2, INF, IL-10, GM-CSF, and/or chemokines, such as M1P1 and RANTES. Immunogens can also be linked to peptides that enhance transport across tissues, as described in O'Mahony, WO 97/17613 and WO 97/17614.

Immunogens of the invention can be linked to carriers by methods including, without exception, chemical crosslinking. Techniques for linking an immunogen to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the e-amino on a lysine, or other free amino group in other amino acids. A variety of such disulfide/amide-forming agents are described by Immun. Rev. 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt.

Peptides included in immunogens of the invention can also be expressed as fusion proteins. The peptide can be linked at the amino terminus, the carboxyl terminus or internally or to the carrier. For example, the peptides may be fused with carriers, or an affinity tag such as poly His or with any useful peptide or protein sequence.

Patients amenable to treatment include individuals at risk of disease but not showing symptoms, as well as patients presently showing symptoms. In the case of certain amyloid diseases including AD, virtually anyone is at risk of suffering from the disease.

Therefore, the present compositions can be administered prophylactically, for example, by a vaccine, to the general population without any assessment of the risk of the subject patient. The present methods are especially useful for individuals who do have a known genetic risk of an amyloid disease, for example, AD. Such individuals may include those having relatives who have experienced an amyloid disease, and those whose risk is determined by analysis of genetic or biochemical markers or who exhibit symptoms or prodromes indicative of the potential for development of, or the actual presence of, such diseases. For example, genetic markers of risk toward AD include mutations in the APP gene, particularly mutations at position 717 and positions 670 and 671 referred to as the Hardy and Swedish mutations respectively (see Hardy, TINS, supra). Other markers of risk for AD are mutations in the presenilin genes, PS1 and PS2, and ApoE4, family history of AD, hypercholesterolemia or atherosclerosis.

Symptoms of amyloid disease are apparent to a physician of ordinary skill. For example, individuals presently suffering from Alzheimer's disease can be recognized from characteristic dementia, as well as the presence of risk factors described above. In addition, a number of diagnostic tests are available for identifying individuals who have amyloid diseases. For example, in the case of AD these include measurement of CSF tau and AB42 levels. Elevated tau and decreased AB42 levels indicate the presence of AD.

In asymptomatic patients, treatment can begin at any age, for example, at the age of 10, 20, 30, 40, 50, 60 or 70. Treatment may entail one or more doses, for example, multiple dosages over a period of time. Treatment can be monitored by assaying antibody, or activated T-cell or B-cell responses to the therapeutic (for example, prefibrillar oligomer mimic) or assaying the levels of oligomer prefibrillar oligomer or protofibrillar aggregate present, each over time. In one embodiment, treatment by administering a single therapeutic of the invention, such as a single immunogen of the invention, may serve as a treatment for or preventive measure against more than one amyloid disease, or at least 2, or at least three, or at least 4, or, for example, all amyloid diseases.

In prophylactic applications, compositions of the invention or medians are administered to a patient susceptible to, or otherwise at risk of, a particular disease in an amount sufficient to eliminate or reduce the risk or delay the outset of the disease. In therapeutic applications, compositions or medians are administered to a patent suspected of, or already suffering from such a disease in an amount sufficient to cure, or at least partially arrest, the symptoms of the disease and its complications. An amount adequate to accomplish this is defined as a therapeutically- or pharmaceutically-effective dose. In both prophylactic and therapeutic regimes, therapeutics are usually administered in several dosages until a sufficient immune response has been achieved. Typically, the immune response is monitored and repeated dosages are given if the immune response starts to fade.

Effective doses of the compositions of the present invention, for the treatment of the above described conditions vary depending upon many different factors, including means of administration, target site, physiological state of the patient, whether the patient is human or animal, other medications administered, and whether treatment is prophylactic or therapeutic. Usually, the patient is a human, but in some diseases, such as mad cow disease, the patient can be a nonhuman mammal, such as a bovine or in the case of Alzheimer's disease, the patient may be a dog. Treatment dosages need to be titrated to optimize safety and efficacy. The amount of immunogen depends on whether adjuvant is also administered, with higher dosages being required in the absence of adjuvant. The amount of an immunogen for administration sometimes varies from about 1 µg to about 500 µg per patient and more usually from about 5 µg to about 500 µg per injection for human administration. Occasionally, a higher dose of about 1 mg to about 2 mg per injection is used. Typically about 10 µg, about 20 µg, about 50 µg or about 100 µg is used for each human injection. The timing of injections can vary significantly from once a day, to once a year, to once a decade. On any given day that a dosage of immunogen is given, the dosage is greater than 1 µg per patient and usually greater than 10 µg per patient if adjuvant is also administered, and greater than 10 µg per patient and usually greater than 100 per patient in the absence of adjuvant. The mass amount of peptide present in the dosage may be used to calculate the quantities of therapeutic used.

One typical regimen consists of an immunization followed by booster injections at 6 weekly intervals. Another regimen consists of an immunization followed by booster injections 1, 2 and 12 months later. Another regimen entails an injection every two months for life. Alternatively, booster injections can be on an irregular basis as indicated by monitoring of immune response.

For passive immunization with an antibody, the dosage ranges from about 0.0001 mg/kg of body weight to about 100 mg/kg of body weight, and more usually about 0.01 mg/kg of body weight to about 5 mg/kg of body weight of the host.

Therapeutics for inducing an immune response can be administered by any suitable means, for example, parenteral, topical, intravenous, oral, subcutaneous, intraperitoneal, intranasal or intramuscular means for prophylactic and/or therapeutic treatment. The most typical route of administration is subcutaneous although others can be equally effective. The next most common is intramuscular injection. This type of injection is most typically performed in the arm or leg muscles. Intravenous injections as well as intraperitoneal injections, intraarterial, intracranial, or intradermal injections may also be effective in generating an immune response. In some methods, therapeutics are injected directly into a particular tissue where deposits have accumulated or may accumulate.

Compositions of the invention can optionally be administered in combination with other agents that are at least partly effective in treatment of amyloidogenic disease. In the case of Alzheimer's and Down's syndrome, in which amyloid deposits occur in the brain, therapeutics of the invention can also be administered in conjunction with other agents that increase passage of the compositions of the invention across the blood-brain barrier.

Immunogenic agents of the invention, such as peptides, are sometimes administered in combination with an adjuvant. A variety of adjuvants can be used in combination with an immunogen of the invention to elicit an immune response. Preferred adjuvants augment the intrinsic response to an immunogen without causing conformational changes in the immunogen that affect the qualitative form of the response. Preferred adjuvants include alum, 3 de-O-acylated monophosphoryl lipid A (MPL). QS21 is a triterpene glycoside or saponin isolated from the bark of the Quillaja Saponaria Molina tree found in South America (see Kensil et al., in *Vaccine Design: The Subunit and Ajuvant Approach* (eds. Powell & Newman, Plenum Press, NY, 1995); and U.S. Pat. No. 5,057,540). Other adjuvants are oil in water emulsions, such as squalene or peanut oil, optionally in combination with immune stimulants, such as monophosphoryl lipid A. See, for example, Stoute et al., *N. Engl. J. Med.* (1997) 336, 86-91. Another useful adjuvant is CpG described in Bioworld Today, Nov. 15, 1998. Alternatively, an immunogen can be coupled to an adjuvant. For example, a lipopeptide version of the immunogen may be prepared by coupling palmitic acid or other lipids directly to the N-terminus of one or more peptides which comprise an immunogen of the invention, as described for hepatitis B antigen vaccination in Livingston, J. Immunol. (1997) 159, 1383-1392. However, such coupling should not substantially change the conformation of the peptides comprising the immunogen so as to affect the nature of the immune response thereto. Adjuvants can be administered as a component of a therapeutic composition with an active agent or can be administered separately, before, concurrently with, or after administration of the therapeutic.

A preferred class of adjuvants is aluminum salts (alum), such as aluminum hydroxide, aluminum phosphate, aluminum sulfate. Such adjuvants can be used with or without other specific immunostimulating agents such as MPL or 3-DMP, QS21, polymeric or monomeric amino acids such as polyglutamic acid or polylysine.

Another class of adjuvants is oil-in-water emulsion formulations. Such adjuvants can be used with or without other specific immunostimulating agents such as muramyl peptides (for example, N-acetylmuramyl-L-threonyl-D-isoglutamine (thr-MDP), -acetyl-normuramyl-L-alanyl-D-isoglutamine (nor-MDP), N-acetylmuramyl-L-alanyl-D-isoglutamyl-L-alanine-2-(1'-2' dipalmitoyl-sn-g-lycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include (a) MF59 (WO 90/14837), containing 5% Squalene, 0.5% Tween 80 and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluroinic-blocked polymer L121, and thr-MDP, either microfluidized into a submicron emulsion or vortexed to generate a larger particle size emulsion, and (c) Ribi™ adjuvant system (RAS), (Ribi Immunochem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™)

Another class of adjuvants is saponin adjuvants, such as Stimulons (QS21, Aquila, Worcester, Mass.) or particles generated therefrom such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins, for example, IL-1, IL-2, and IL-12, macrophage colony stimulating factor (M-CSF), tumor necrosis factor (TNF) and/or chemokines such as CXCL10 and CCL5.

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the vaccine containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Optionally, two or more different adjuvants can be used simultaneously. Preferred combinations include alum with MPL, alum with QS21, MPL with QS21, and alum, QS21 and MPL together. Also, Incomplete Freund's adjuvant can be used (Chang et al., Advanced Drug Delivery Reviews 32, 173-186 (1998)), optionally in combination with any of alum, QS21, and MPL and all combinations thereof.

Compositions of the invention may be administered as pharmaceutical compositions comprising a variety of other pharmaceutically acceptable components. See *Remington's Pharmaceutical Science* (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. However, some reagents suitable for administration to animals, such as complete Freund's adjuvant are not typically included in compositions for human use.

Pharmaceutical compositions can also include large, slowly metabolized macromolecules such as proteins, polysaccharides, polylactic acids, polyglycolic acids and copolymers (such as latex functionalized sepharose, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, compositions of the invention can be administered as injectable dosages of a solution or suspension of the substance in a physiologically acceptable diluent with a pharmaceutical carrier which can be a sterile liquid such as water oils, saline, glycerol, or ethanol. Auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Compositions of this invention may be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. See Langer, Science (1990) 249, 1527 and Hanes, Advanced Drug Delivery Reviews (1997) 28, 97-119. The compositions of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient In the range of 0.5% to about 10%, for example, about 1% to about 2%. Oral formulations commonly include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and may contain about 10% about 95% of active ingredient, for example, about 25% to about 70%.

Topical application can result in transdermal or intradermal delivery. Topical administration can be facilitated by co-administration of the composition with cholera toxin or detoxified derivatives or subunits thereof or other similar bacterial toxins. See Glenn et al., *Nature* (1998) 391, 851. Co-administration can be achieved by using the components as a mixture or as linked molecules obtained by chemical crosslinking or expression as a fusion protein.

Alternatively, transdermal delivery can be achieved using a skin path or using transferosomes. See for example, Paul et al., *Eur. J. Immunol.* (1995) 25, 3521-24; Cevc et al., *Biochem. Biophys. Acta* (1998) 1368, 201-15.

The invention provides methods of detecting an immune response against amyloid oligomeric intermediates in a patient suffering from or susceptible to amyloid diseases such as AD. The methods are particularly useful for monitoring a course of treatment being administered to a patient. The methods can be used to monitor both therapeutic treatment on symptomatic patients and prophylactic treatment on asymptomatic patients.

Some methods entail determining a baseline value of an immune response in a patient before administering a dosage of composition, and comparing this with a value for the immune response after treatment. A significant increase (i.e., greater than the typical margin of experimental error in repeat measurements of the same sample, expressed as one standard deviation from the mean of such measurements) in value of the immune response signals a positive treatment outcome (i.e., that administration of the composition has achieved or augmented an immune response). If the value for immune response does not change significantly, or decreases, a negative treatment outcome is indicated. In general, patients undergoing an initial course of treatment with a composition are expected to show an increase in immune response with successive dosages, which eventually reaches a plateau. Administration of composition is generally continued while the immune response is increasing. Attainment of the plateau is often an indicator that the treatment can be discontinued or reduced in dosage or frequency.

In other methods, a control value (i.e., a mean and standard deviation) of immune response is determined for a control population. Typically the individuals in the control population have not received prior treatment. Measured values of immune response in a patient after administering a therapeutic composition are then compared with the control value. A significant increase relative to the control value (for example, greater than one standard deviation from the mean) signals a positive treatment outcome. A lack of significant increase or a decrease signals a negative treatment outcome.

Administration of composition is generally continued while the immune response is increasing relative to the control value.

As before, attainment of a plateau relative to control values in an indicator that the administration of treatment can be discontinued or reduced in dosage or frequency.

In other methods, a control value of immune response (for example, a mean and standard deviation) is determined from a control population of individuals who have undergone treatment with a therapeutic composition and whose immune responses have plateaued in response to treatment. Measured values of immune response in a patient are compared with the control value. If the measured level in a patient is not significantly different (for example, more than one standard deviation) from the control value, treatment can be discontinued. If the level in a patient is significantly below the control value, continued administration of composition is warranted. If the level in the patient persists below the control value, then a change in treatment regime, for example, use of a different adjuvant may be indicated.

In other methods, a patient who is not presently receiving treatment but has undergone a previous course of treatment is monitored for immune response to determine whether a resumption of treatment is required. The measured value of immune response in the patient can be compared with a value of immune response previously achieved in the patient after a previous course of treatment. A significant decrease relative to the previous measurement (e.g., greater than a typical margin of error in repeat measurements of the same sample) is an indication that treatment can be resumed. Alternatively, the value measured in the patient can be compared with a control value (mean plus standard deviation) determined in population of patients after undergoing a course of treatment.

Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (e.g., more than a standard deviation) is an indicator that treatment should be resumed in a patient.

Depending upon the disease, tissue samples from different tissues may be used. For example, the tissue sample for analysis is, without limitation, typically blood, plasma, serum, mucus or cerebral spinal fluid from the patient. The sample may be analyzed for indicia of an immune response to an amyloid peptide aggregate or an amyloid peptide aggregate mimic. The immune response can be determined from the presence of, for example, antibodies or T-cells that specifically bind to an amyloid peptide aggregate or amyloid peptide aggregate mimic. ELISA methods of detecting antibodies specific to compositions are described in the Examples section.

The invention further provides diagnostic kits for performing the diagnostic methods described above. Typically, such kits contain a composition that specifically binds to antibodies having specificity or selectivity to prefibrillar oligomers or that reacts with T-cells specific for prefibrillar oligomers. The composition may contain one or more of the constrained, prefibrillar oligomer-like antigenic peptides of the invention. The kit can also include a label. For detection of antibodies to amyloid peptide aggregates, the label is typically in the form of labelled anti-idiotypic antibodies. For detection of antibodies, the composition can be supplied prebound to a solid phase, such as to the wells of a microtiter dish. For detection of reactive T-cells, the label can be supplied comprising $^3$H-thymidine to measure a proliferative response. Kits also typically contain directions for use of the kit. The directions may also include a chart or other correspondence regime correlating levels of measured label with levels of antibodies to oligomeric intermediates or T-cells reactive with oligomeric intermediates.

EXAMPLE 1

Synthesis of Molecular Mimics of Amyloid Peptide Aggregates Peptide Synthesis

Solid phase synthesis and purification of AB40 (SEQ ID NO 1), AB42 (SEQ ID NO 2), IAPP (SEQ ID NO 3) and human prion 106-126 (SEQ ID NO 4), Polyglutamine KKQ40KK (SEQ ID NO: 5), Random Sequence #2A (SEQ ID NO:10), Random Sequence #3A (SEQ ID NO: 11), Random Sequence #3B (SEQ ID NO: 12) and Random Sequence #4B (SEQ ID NO: 13) is carried out by fluoren-9-ylmethoxy carbonyl chemistry using a continuous flow semiautomatic instrument as described previously by D. Burdick et al. (1992) *J Biol Chem* 267, 546-54. C-terminal thioester by Fmoc chemistry IS carried out essentially as described in Inginito, R. et al., (1999) *Journal of the American Chemical Society* 121, 11369-11374.

For each peptide, the first amino acid is manually coupled to the sulfamylbutyry-AM-PEGA resin (Novabiochem, San Diego, Calif.), 1 g of resin in 10 mL of dichloro methane (DCM), 5 equivalents of the first (carboxy terminal) amino acid is added (Fmoc-Ala-OH for AB42), (Fmoc-Val-OH for AB40, Random Sequence #3A and Random Sequence #3B), (Fmoc-Tyr(t-But)-OH for IAPP), (Fmoc-Thr for Random Sequence #2A), Fmoc-Lys for Polyglutamine KKQ40KK (SEQ ID NO: 5)), (Fmoc-Ile for Random Sequence #4B), followed by the addition of 10 equivalents of diisopropylethylamine (DIEA). The mixture is stirred for 20 min at room temperature, then cooled to (−10 to −20° C.). 4.7 equivalents of ByBop (benzotriazol-1-yl-oxy-tris(pyrrolidino)-phosphonium hexafluorophosphate) is added and the mixture stirred for 8 to 9 hours at −10 to −20° C. The coupling efficiency is checked using the Kaiser test, which is well known in the art of peptide synthesis, and the substitution level is around 0.18- to 0.20 mmole/g, as is determined using the Fmoc cleavage method. Acetylation is performed using acetic anhydride. The amino acid chain is elongated by fluoren-9-ylmethoxy carbonyl chemistry using a continuous flow semiautomatic instrument. 100 mg of peptide is washed with N-methyl-2-pyrrolidone 5×(NMP) 5.0 mL of NMP, 185 µL of i-Pr2EtN (1.1 mmol), and 400 µL of iodoacetonitrile (previously filtered through an alumina basic filter bed in the dark) in a synthesis vessel. The reaction mixture is shaken for 24 h in the dark on a rotary plate. The resin is washed with 5× with NMP and 5×DMF followed by a wash using 5×CH2C12 and then dried. 100 mg of resin is washed with 5×THF, followed by the addition of 2.7 mL THF. 2.7 mL of TMS-CH2N2 (50:50, v/v, hexane) is then added. After stirring for 2 h, the resin is washed with 5×5 mL THF and 5×5 mL DMF.

The resin is added to 120 µL of ethyl-3-mercaptopropionate and the mixture is shaken on a rotary plate for 24 h.

The resin is filtered then washed with 3×3 ml DMF. The filtrate and washes are collected, rotary evaporated at 34° C. The yields are about 60%.

The resulting peptides are deprotected using standard methods (TFA and scavengers), and purified by RP-HPLC. The purity is checked by analytical RP-HPLC and electrospray mass spectrometry.

Human insulin, lysozyme, and α-synuclein are obtained from commercial or other sources.

A C-terminal thioester is attached to each of these synthesized and commercial peptides in a conventional manner.

Assembly of Colloidal Gold Amyloid Oligomer Molecular Mimic:

Colloidal gold nanospheres (mean diameter of 5.3 nm) are purchased from Ted Pella, Inc. and washed with 1 M HCL followed by three washings in distilled water. The gold nanospheres are incubated in a solution of 0.2 mg/ml of each C-terminal thioester peptide, pH (5.0-5.5) for 3 h. The pH is then adjusted to 7.4 with 100 mM Tris pH 8.0 (0.2% sodium azide).

After incubation for 6 h at room temperature, the antigen is collected by centrifugation at 30,000×G at 4° C. for 30 min, washed three times with PBS pH 7.6 to remove unincorporated peptide and then dispersed in 0.02% sodium azide.

The resulting micelle molecular mimics are analyzed by atomic force microscopy (AFM), circular dichroism spectroscopy, thioflavin T fluorescence, bis-ANS fluorescence, and UV/visible spectroscopy to confirm that the peptide monolayer on the gold has the same secondary structure and conformation as the oligomeric amyloid intermediates display in solution. The solutions are stored at 4° C.

A schematic view of the assembly of a molecular mimic is shown in FIG. 1.

EXAMPLE 2

Production of Antibodies to Colloidal Gold Amyloid Oligomer Molecular Mimics

New Zealand white rabbits are injected with a quantity of a molecular mimic produced as described in Example 1 corresponding to about 0.08 to about 1.0 mg of the relevant peptide. Each gold-conjugated antigen is mixed with incomplete Freund's adjuvant, alum adjuvant or with no adjuvant (PBS only) prior to injection. The rabbits are immunized with 1 mL of the antigen (0.08-0.1 mg of peptide per rabbit, dialyzed against PBS at 4° C., overnight). For the first injection, equal parts antigen and complete Freund's adjuvant are used. For the subsequent 11 injections, the antigen is mixed with incomplete Freund's adjuvant and each are injected at 2-week intervals. Animals are injected subcutaneously in small increments of 0.1 mL per site in a checkerboard fashion on the scapular region.

Serum is collected by venipuncture. The IgG fraction is affinity purified on Protein G-Sepharose beads, eluted in 0.2 M glycine, pH 2.2, neutralized with Tris buffer to pH 7.4 and then dialyzed against PBS, pH 7.4. The intermediate aggregate-specific antibodies (termed oligomer antibodies) are purified by adsorption on the amyloid oligomeric intermediate molecular mimics by mixing the molecular mimics with the IgG fraction and incubating for 2 h, followed by washing. The oligomeric intermediate specific antibodies are eluted in 0.2 M glycine, pH 2.2, followed by neutralization and dialysis against PBS. The isolated polyclonal antibody preparation is stored in PBS containing 0.02% sodium azide as preservative at 4° C. or at −70° C.

The polyclonal serum produced by vaccination of rabbits with the molecular mimics is selective or specific for the amyloid peptide aggregate intermediates and is not detectably reactive with soluble low molecular weight or fibrillar amyloid peptide species comprising the same monomer peptide. Surprisingly, no anti-oligomer immunoreactivity was observed for the unfractionated serum against low molecular weight Aβ or Aβ fibrils even after boosting the rabbits twelve times, indicating that the immune response to the molecular mimics is very specific.

Monoclonal antibodies are made essentially as disclosed in Glabe & Kayed, International Patent Publication No. WO 20050255016. This application and the disclosure of U.S. Patent Publication No. US 20060280733 are incorporated by reference herein in their entirety.

One polyclonal antibody preparation raised using Aβ peptide joined to colloidal gold as an immunogen, as described above, was found to specifically bind prefibrillar oligomers comprising either A840 peptide (SEQ ID NO: 1) or Aβ42 peptide (SEQ ID NO: 2), or lysozyme (SEQ ID NO: 6). This polyclonal antibody preparation was termed A-11. Antibody A-11 was also determined not to bind to soluble monomeric or low MW Aβ40, Aβ42 or lysozyme peptide monomers or small molecular weight homopolymers, or to Aβ40, Aβ42 fibrils or lysozyme fibrils or large molecular weight aggregates or tangles.

Polyclonal antibody preparations were made using IAPP (SEQ ID NO: 3) thioester monomers joined as a molecular mimic to a colloidal gold particle as the antigen. The antigen was injected into rabbits as described above, and the rabbit serum enriched as described above. The new anti-IAPP antibody preparation was termed 1-11.

EXAMPLE 3

Production of Low Molecular Weight Aggregates, Oligomeric Intermediates And Mature Amyloid Fibrils Monomeric or low molecular weight aggregates, oligomeric intermediates and mature amyloid fibrils may be produces as described in this example or as reported in Kayed et al., *Science* 300:486-489 (2003); Kayed et al., *J. Biol. Chem.* 279:46363-6 (2004); and Kayed & Glabe, *Meth. Enzym.* 413:326-344 (2006), each of which is hereby incorporated by reference herein in its entirety.

Preparation of Monomer and Low Molecular Weight Aggregates:

Monomeric Aβ42, α-synuclein and peptide 3A peptides and their low molecular weight polymeric species are prepared by dissolving 1.0 mg 0.3-0.6 mg of each lyophilized peptide in 700 μl HFIP (hexafluoroisopropanol) at room temperature.

A monomer and low molecular weight amyloid peptide preparation is made from the freshly prepared peptide solution.

Soluble prefibrillar oligomers are made from dissolved amyloid peptides by stirring the solutions for 2-3 days in a fume hood at room temperature.

Fibrils are made from amyloid peptides by stirring the solutions for 7-9 days in the fume hood at room temperature. A 100 μL quantity of the resulting peptide solution is added to 900 μL DD $H_2O$ in a siliconized Eppendorf tube. After 10-20 min incubation at room temperature, the samples are centrifuged for 15 min at 14,000×g and the supernatant fraction (pH 2.8-3.5) is transferred to a new siliconized tube and subjected to a gentle stream of $N_2$ for 5-10 min to evaporate the HFIP. The samples are then used immediately or fractionated by gel permeation to remove any larger molecular weight fibrils or oligomeric intermediates.

Preparation of Prefibrillar Oligomers:

Aβ42, α-synuclein and peptide 3A amyloid peptide aggregates (prefibrillar oligomers) are prepared essentially as follows. 1.0 mg of each peptide monomer was dissolved in 400 μL HFIP for 10-20 min at room temperature. 100 μL of the resulting monomer solution is added to 900 μL DD $H_2O$ in a siliconized Eppendorf tube. After 10-20 min incubation at room temperature, the samples are centrifuged for 15 min at 14,000×g and the supernatant fraction is transferred to a new siliconized tube and subjected to a gentle stream of $N_2$ for 5 to 10 min to evaporate the HFIP. The samples are stirred at 500 RPM using a Teflon coated micro stir bar for 24 to 48 h at 22° C. In order to prepare highly pure samples of peptide intermediates, residual trifluoroacetate ions are removed by lyophilization in 1 mM HCl followed by lyophilization in 50% acetonitrile.

The time of stirring required to obtain an optimum level of intermediates (prefibrillar oligomers) depends on subtle factors, which will be apparent to those of ordinary skill in the art, including the speed of stirring and the peptide concentration. The highest level of intermediates for each monomer was recovered after between 6 hrs and 3 days of stirring. Generally we have found that fibrils are formed after 7-9 days of stirring, oligomers after 2-3 days of stirring, and monomers are optionally found when freshly dissolved.

The amount of oligomeric intermediates and monomer or low molecular weight aggregates is monitored carefully using A-11 antibody and confirmed by electron microscopy.

Purification of the intermediates from fibrils is done by centrifugation at 100,000×g for 1 h. Monomeric or low molecular weight aggregates are removed by application of the supernatant to a gel permeation chromatography column. Intermediates are eluted near the void volume of the column and the monomer and low molecular weight aggregates elute near the included volume and are discarded.

Preparation of Fibrils:

Homomeric fibrils comprising Aβ42, α-synuclein and peptide 3A are prepared under three different conditions, water (pH 3.8 to 4.2) containing 0.02% sodium azide. The final peptide concentration in each preparation is 0.3 mg/ml (approximately 80-125 μM). The samples are stirred with a Teflon coated micro stir bar at 500 rpm at room temperature for 6 to 9 days. Fibril formation is monitored by thioflavin T fluorescence and UV light scattering. Once fibril formation is complete, the solutions are centrifuged at 14,000×g for 20 min, the fibril pellet is washed 3× with doubly distilled water and then resuspended in the desired buffer. The presence of mature fibril morphology and the absence of spherical oligomeric intermediates and protofibrils is verified by AFM or negative stain EM.

EXAMPLE 4

Assessment of Potential Therapeutic Activity

The various amyloid peptide preparations are examined by screening against A-11 antibody preparation using dot blot analyses and ELISA assays.

Additionally, 4 mg of gold-coupled peptide 3A was used to vaccinate two New Zealand rabbits, termed 1539 and 1540. The rabbits there vaccinated and boosted twice using 0.25 mg antigen per rabbit. Both pre-immunization (prebleed) serum and post-boost immune serum was collected from each rabbit.

Dot Blot Assay

Figure 2:
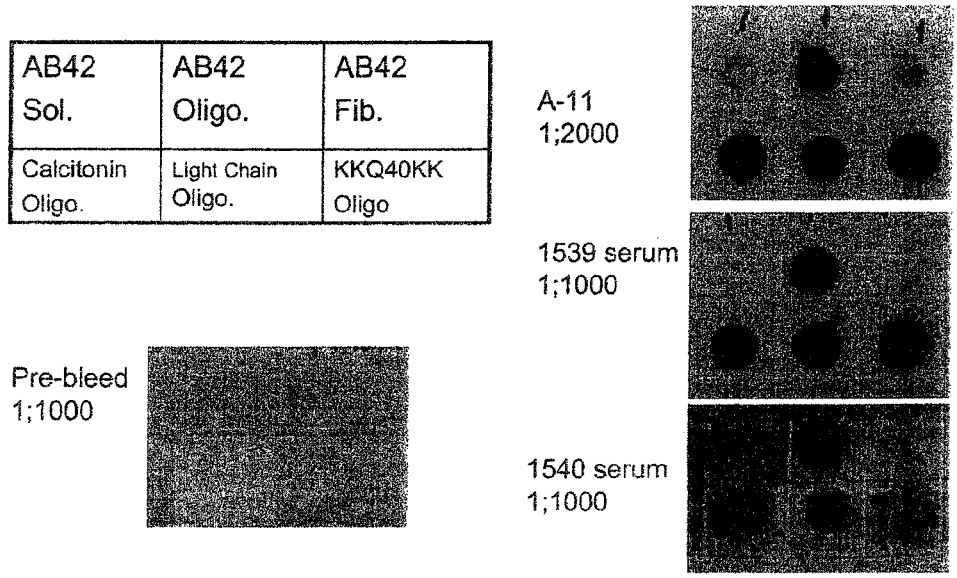
FIG. 2 shows the result of a dot blot assay where Aβ monomers, Aβ prefibrillar oligomers, Aβ fibrils, calcitonin soluble prefibrillar oligomers, IgG lambda light chain soluble prefibrillar oligomers, and KKQ40KK (SEQ ID NO: 5) soluble prefibrillar oligomers are spotted to a nitrocellulose membrane and are probed with A-11 (a polyclonal antibody preparation), and antiserum from rabbits [1539 and 1540] immunized against Peptide 3A. Dot blots were incubated with film for 10 minute, then the film was developed. It is noteworthy that the immune response to the 3A peptide antigen is substantially similar if not identical to the immune response to the Aβ peptide antigen.
Figure 3:
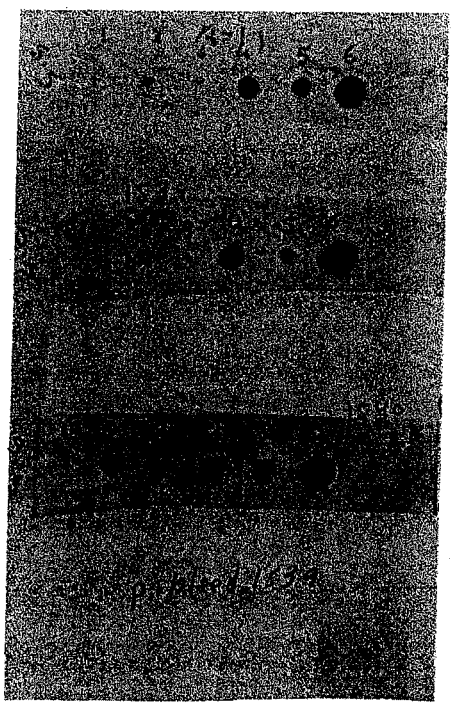
FIG. 3 shows the result of a dot blot assay where Aβ monomers, Aβ prefibrillar oligomers, Aβ fibrils, a preparation of α-synuclein, soluble prefibrillar oligomers, prions (e.g., human prion 106-126), soluble prefibrillar oligomers, and insulin soluble prefibrillar oligomers are spotted to a nitrocellulose membrane and are probed with A-11 (a polyclonal antibody preparation), and antiserum from rabbits [1539 and 1540] immunized against Peptide 3A. Dot blots were incubated with film for 10 minutes, then the film was developed. It is noteworthy that the immune response to the 3A peptide antigen is substantially similar if not identical to the immune response to the Aβ peptide antigen.

Monomeric or low molecular weight aggregates, oligomeric intermediates and amyloid fibrils are prepared as describe in Example 3 and each dissolved in DD $H_2O$ at a concentration of 0.5 mg/ml immediately before use. One μl of a solution or suspension of each amyloid species as indicated in FIG. 2, FIG. 3. and FIG. 4 was spotted onto each of 4 nitrocellulose filters. Each membrane was blocked with 10% non-fat milk in Tris-buffered saline (TBS) containing 0.01% Tween 20 (TBS-T), at room temperature for 1 h. Each membrane was then washed three times for 5 min each with TBS-T; membranes were then incubated for 1 hr at room temperature with either affinity-purified anti-oligomer A-11 antibody preparation (diluted 1:2000 in 3% BSA in TBS-T or with a polyclonal rabbit serum (1539 or 1540)); or a pre-bleed serum (diluted 1:1,000 in 5% milk solution).

The membranes were incubated for 1 hour with shaking at room temperature, washed three times for 5 min each with TBS-T, then incubated with secondary antibody goat anti-rabbit diluted 1:10000 in 5% milk solution for one hour at room temperature with shaking. Membranes were again washed three times for 5 min each with TBS-T. 1-2 ml of a standard ECL (enhanced chemiluminescence) western blotting detection reagent was used for detection with each membrane. Films were then developed for 1 minute and 10 minutes.

FIG. 2 shows the results of a 10 minute exposure of a dot blot experiment in which monomeric and low molecular weight Aβ42 (Aβ42 sol.), prefibrillar Aβ42 aggregates (Aβ42 oligo) and Aβ fibrils (Aβ42 fib.) were spotted onto a nitrocellulose filter along with the oligomeric prefibrillar oligomers of calcitonin, light chain lambda chain (which is found in all Ig classes, not just IgG), and polyglutamine synthetic peptide KKQ40KK (SEQ ID NO: 5), and are probed with A-11 (a polyclonal antibody preparation), and antisera from rabbits 1539 and 1540 immunized against Peptide 3A.

It can be seen in FIG. 2 that antibody A-11 only recognizes the soluble aggregate intermediates of Aβ42, calcitonin, IgG kappa light chain peptide and the synthetic polyglutamine peptide, while A-11 does not bind either the monomeric form of Aβ42 or the fibrils of aβ42.

Both rabbit anti-peptide 3A serum preparations 1539 and 1540 show exactly the same selectivity. The soluble monomeric amyloids and insoluble fibrils are not detected by either rabbit polyclonal preparation. However, oligomeric intermediates of Aβ42, calcitonin, Ig lambda light chain peptide, and polyglutamine synthetic peptide are all detected by both rabbit serum.

Similar membranes are prepared as indicated above as strips in quadruplicate; these membranes were spotted with the Aβ42 amyloid forms used in FIG. 2; additionally, 1 μl each of soluble prefibrillar oligomers of α-synuclein, human prion$_{106-126}$ and insulin peptides were also used. Again, the membranes were probed with either the A-11 antibody preparation, rabbit 1539 anti-peptide 3A serum, rabbit 1540 anti-peptide 3A serum, or pre-bleed serum and developed using the ECL reagent. Films were exposed for 10 minutes.

The results are shown in FIG. 3, and are similar to those seen in FIG. 2. All antibodies show the same selectivity or specificity towards soluble prefibrillar amyloid oligomers, irrespective of the primary amino acid sequences of the peptide. Additionally, all tested antibody preparations fail to detect low molecular weight preparations of Aβ42 or Aβ42 fibrils.

ELISA Assay

Samples comprising the following amyloid peptide forms were applied to a 96 well plate and analyzed by ELISA using A-11 and anti-peptide 3A antibody preparations made as indicated in Example 2.

ELISA plates were coated with 200 ng, 100 ng, 50 ng, 25 ng, 12.5 ng, 6.25 ng, 3.62 ng, and 1.81 ng of each antigen per well in a volume of 100 µl using coating buffer (0.1 M sodium bicarbonate, pH 9.6), and incubated for 2 hours at 37 C. The wells were then washed 3× using plate washer solution (Bio-Rad), then blocked with 5% bovine serum albumin (BSA) in TBS-T for 1 hour at 37 C. Plates were washed 3× with TBS-T.

Antibody was applied to each well in a volume of 100 µl; A-11 antibody was diluted 1:2000 in 5% milk in TBS-T, while the serum from rabbits 1539 and 1540 was diluted 1:1000 in 5% milk in TBS-T. Secondary antibody (horseradish peroxidase (HRP)-conjugated anti-rabbit diluted 1:10000 in 5% milk in TBS-T) was added in a volume of 100 µl and permitted to incubate for 1 hour 37 C. Plates were then washed 3× with TBS-T.

ELISA plates were developed using 100 µl per well of a chromogenic HRP substrate TMB (3",5,5"-tetramethylbenzidine) in an acidic solution; this was incubated at room temperature until color development (20-30 min). The reaction was stopped using 0.5HCl and the absorbance of each well read at 450 nm.

Figure 4A:
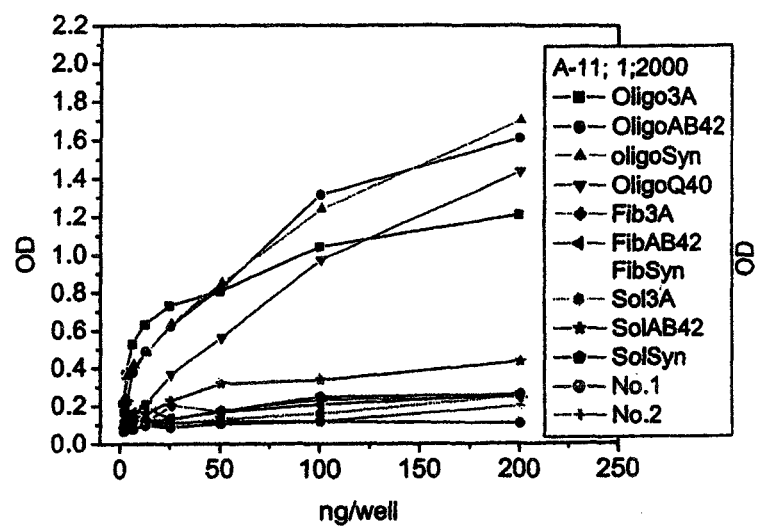
FIG. 4 shows the results of an ELISA assay where monomeric (Sol), prefibrillar oligomers (Oligo) and fibrillar (Fib), preparations of 3A peptide, Aβ42, alpha synuclein and polyglutamine synthetic peptide KKQ40KK (SEQ ID NO: 5) are analyzed for anti-oligomer specificity using serum from 3A oligomer mimic vaccinated rabbit 1540 (Right panel) and A-11 antibody preparation from a rabbit vaccinated with Aβ oligomer mimic (Left panel). No. 1 and No 2 are controls omitting the primary and secondary antibodies, respectively.
Figure 4B:
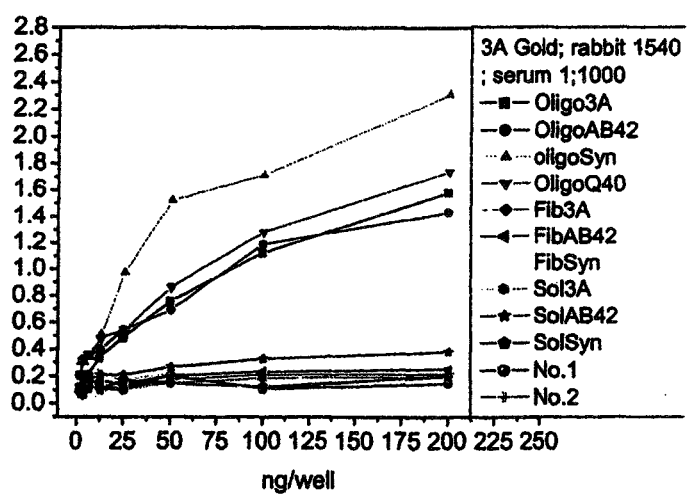
Figure 5A:
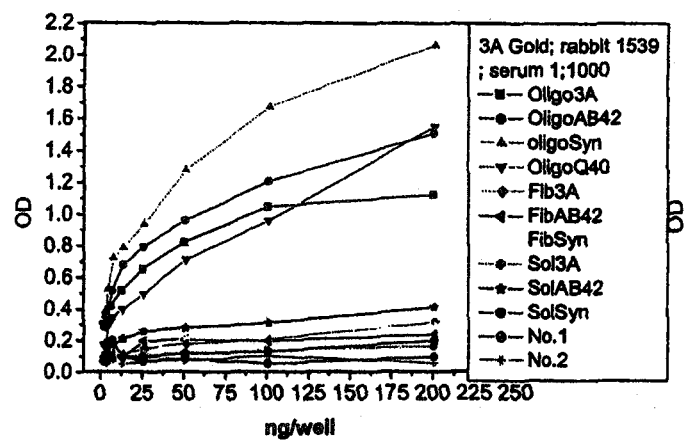
FIG. 5 shows the results of an ELISA assay where monomeric (Sol), prefibrillar oligomers (Oligo) and fibrillar (Fib), preparations of 3A peptide, Aβ42, alpha synuclein and polyglutamine synthetic peptide KKQ40KK (SEQ ID NO: 5) are analyzed for anti-oligomer specificity using serum from 3A oligomer mimic vaccinated rabbit 1539 (Left panel) and A-11 antibody preparation from a rabbit vaccinated with Aβ oligomer mimic (Right panel). No. 1 and No. 2 are controls omitting the primary and secondary antibodies, respectively.
Figure 5B:
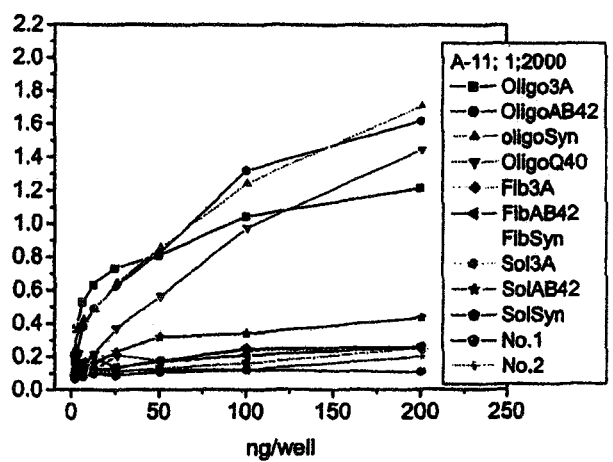

The resulting data is showing in FIGS. 4 and 5. In FIG. 4 the left panel shows that the A-11 antibody binds the oligomeric (prefibrillar oligomers) form of each peptide tested (Random peptide 3A, Aβ42, α-synuclein and synthetic peptide KKQ40KK (SEQ ID NO: 5)) with a significant dose-response curve. By contrast, the low molecular weight and fibril forms of the tested peptides (Random peptide 3A, Aβ42, and α-synuclein) only bind the A-11 antibody at background levels.

In FIG. 4, the right panel shows that the serum from rabbit 1540 inoculated with gold-bound Random Peptide 3A shows similar results as seen with A11 in the left panel; all oligomeric forms of the tested peptides bind the 1540 antibody preparation, while both monomeric and low molecular weight forms and fibril forms of the peptides are not bound appreciably by the rabbit 1540 anti-3A antibody preparation.

In FIG. 5 the serum from rabbit 1539 inoculated with gold-bound Random Peptide 3A shows similar results as seen in FIG. 4; all oligomeric forms of the tested peptides bind the 1539 antibody preparation (left panel), while both monomeric and low molecular weight forms and fibril forms of the peptides are not bound appreciably by the rabbit 1539 anti-3A antibody preparation.

EXAMPLE 5

Method of Diagnosis Using an ELISA Assay

Cerebrospinal fluid samples are diluted serially at two-fold dilutions in coating buffer (0.1 M sodium bicarbonate, pH 9.6). 100 µl of the samples are added to wells of 96-well microplates, incubated for 2 hours at 37° C., washed three times with (PBS containing 0.01% Tween 20, PBS-T) and then blocked for 2 h at 37° C. with 3% BSA TBS-T. The BSA used is IgG free (Sigma). The plates are then washed three times with PBS-T and 100 µl of a 1:10,000 dilution of an anti-oligomer antibody preparation (raised against a random peptide containing alternating polar and non-polar amino acid residues predicted to form a β-sheet structure under physiological conditions) in 3% BSA/TBS-T is added and incubated for 1 hour at 37° C. The plates are washed three times with PBS-T and 100 µl horseradish peroxidase-conjugated anti-rabbit IgG (Promega diluted 1:10,000 in 3% BSA TBS-T) is added and incubated for 1 hour at 37° C. The plates are washed three times with PBS-T and developed using 3,3',5,5'-tetramethylbenzidine (TMB; KPL Gaithersburg, Md.). The reaction is stopped with 100 µL 1 M HCl and the plates read at 450 nm. Binding of the anti-oligomer antibody to the ELISA plate wells indicates the presence of amyloid oligomeric intermediate.

EXAMPLE 6

Method for Assessing Efficacy of a Treatment Method

The oligomer specific antibody can be utilized in screening for drugs and therapeutic agents that inhibit the formation of amyloid oligomeric intermediates or cause the disassembly or disaggregation of such oligomeric intermediates. In order to screen for drugs that inhibit amyloid oligomer intermediate formation, a test compound or drug is incubated with a random peptide containing alternating polar and non-polar amino acid residues predicted to form a β-sheet structure under physiological conditions in which amyloid oligomeric intermediates form in the absence of any inhibitory effect. The mixture is assayed by ELISA plates essentially as described in Example 4 determining the amount of amyloid oligomeric intermediates formed. In order to test for compounds, that disassemble or disaggregate oligomeric intermediates, preformed oligomeric intermediates are mixed with a test drug or compound and the mixture is assayed by ELISA determining the amount of oligomeric intermediates present. An inhibitory compound gives rise to a lower amount of amyloid oligomers detected by anti-oligomer antibody in the assay.

EXAMPLE 7

Vaccination of Amyloid Protein Precursor (APP) Transgenic Mice (Tg2576 Mice) Improves Cognitive Function Independent of the Peptide Antigen Sequence In this example, APP transgenic mice (Tg2576) are shown to demonstrate improved cognitive function following monthly vaccination with gold-coupled generic amyloid peptide vaccines irrespective of the particular peptide antigen sequence employed.

Preparation of Peptides and Coupling with Gold

Lyophilized Aβ1-40 peptides were resuspended in 50% acetonitrile in water and re-lyophilized. Soluble oligomers were prepared by dissolving 1.0 mg of peptide in 400 µL hexafluoroisopropanol (HFIP) for 10-20 min at room temperature. 100 µl of the resulting seedless solution was added to 900 µl MilliQ $H_2O$ in a siliconized Eppendorf tube. After 10-20 min incubation at room temperature, the samples were centrifuged for 15 min. at 14,000×G and the supernatant fraction (pH 2.8-3.5) was transferred to a new siliconized tube and subjected to a gentle stream of $N_2$ for 5-10 min to evaporate the HFIP. The samples were then stirred at 500 RPM using a Teflon coated micro stir bar for 24-48 hr at 22° C. Oligomers were validated by atomic force microscopy (AFM), electron microscopy (EM) and size exclusion chromatography (SEC) as described [Kayed et al., 2003]. Fibrils were formed by dissolving the lyophilized Aβ1-42 in 50%

HFIP and stirred with closed caps for 7 days. Solution is stirred again for 2 days using open caps to evaporate the HFIP. Fibrils were sedimented and washed in PBS, and resuspended at 2 mg/ml. For the oligomer antigen (oligo), Aβ oligomer molecular mimic was prepared by conjugating Aβ40 via a carboxyl terminal thioester to 5 nm colloidal gold as previously described [Kayed et. al., 2006], same procedure was used for IAPP oligomers and products were stored at 4° C. until used. In addition we also developed a synthetic antigen (3A) that is used as a non human random peptide sequence to minimize the potential for autoimmune inflammatory side effects. This random peptide was also coupled to the colloidal gold (Kayed et al., 2006).

Immunization of Test Animals

Tg2576 mice are a widely used strain that exhibit extracellular Aβ deposits and cognitive deficits. The mice were randomly assigned to treatment groups of 6 animals per group and each group was immunized with one of the following: Aβ Oligomers, IAPP Oligomers, Aβ Fibrils, Random peptide (3A) Oligomer or PBS control.

Immunization was done every month. Briefly, the antigens were mixed with incomplete Freunds adjuvant (1:1 v/v). The immunization was done subcutaneously (100 μg/immunization). Immunization controls include injection of adjuvant with PBS only (no peptide antigen).

Behavioral Studies

Animals were tested at 6 months, 10 months and 14 months of age. Hidden and cued platform Morris water maze (MWM) and Object recognition tests were conducted.

Morris Water Maze Study

Morris Water Maze is a special memory task related with hippocampus (Billings L. M et al., 2005). The apparatus used for all water maze tasks was a circular aluminum tank (1.5 m diameter) painted white and filled with water maintained at 26° C.-29° C. The maze was located in a room containing simple visual, extramaze cues. To reduce stress, mice were placed on the platform in both the hidden and cued versions of the task for 15 seconds prior to the first training trial. Mice were trained to swim to a circular clear Plexiglas platform (14 cm diameter) submerged 1.5 cm beneath the surface of the water and invisible to the mice while swimming. The platform location was selected randomly for the tests at the 6 and 10 month time points but was kept constant for each individual mouse throughout training. On each trial, the mouse was placed into the tank at one of four designated start points in a pseudorandom order. Mice were allowed 60 seconds to find the submerged platform. If a mouse failed to find the platform within 60 seconds, it was manually guided to the platform and allowed to remain there for 15 seconds. After this, each mouse was placed into a holding cage under a warming lamp for 30 seconds before beginning the next trial. To ensure that memory differences were not due to lack of task learning, mice were given four trials a day for as many days as were required to train the Tg2576 and 3xTg-AD-h mice to reach the criterion (<20 seconds). To control for overtraining, probe trials were run for each group, both as soon as they reached group criterion and after all groups had reached criterion. We trained the Tg2576 for 8 days both during 6 month and 10 month, the 3xTg-AD-h mice met the criterion in 5 days. Retention of the spatial training was assessed 1.5 hr and again 24 hr after the last training trial. Both probe trials consisted of a 60 s free swim in the pool without the platform. Mice were monitored by a camera mounted in the ceiling directly above the pool to record the 1.5 hr and 24 hr test. The parameters measured during the probe trial included (1) initial latency to cross the platform location, (2) number of platform location crosses, and (3) time spent in the quadrant opposite to the one containing the platform during training For the 10 months and 14 months training, the location of platform was changed to avoid "savings" from previous water maze experience.

Object Recognition Study

Object recognition tasks are more dependent on the cortical region of the brain than are special memory tasks of the type tested by the above-described water maze study. In this object recognition study, each mouse was placed in the chamber with two identical objects spaced ≅12 inches apart. The animals were allowed to explore the objects for 5 min. After a 5 min retention interval in which the animal was returned to its home cage, the mouse was placed back in the chamber with the previously exposed object and a novel object for a 3 min probe test.

Passive Avoidance Study

Contextual learning and memory was evaluated using the passive inhibitory avoidance task, performed in the Gemini Avoidance System (San Diego Instruments, San Diego, Calif.). The training trial consisted of placing a mouse in the illuminated compartment of the device, and recording the time required for it to enter the dark compartment (baseline latency). Upon entering, the door between the two compartments was closed and the animal was immediately given an electric shock to the feet (0.15 mA, 1 s). During the retention trials (conducted 1.5 h and 24 h after the training trial), the mouse was again placed in the illuminated compartment and the latency to enter the dark compartment was recorded. The retention trial was interrupted if the animal took more than 180 s to cross into the dark compartment.

Results

Morris Water Maze-Results

Figure 6A:
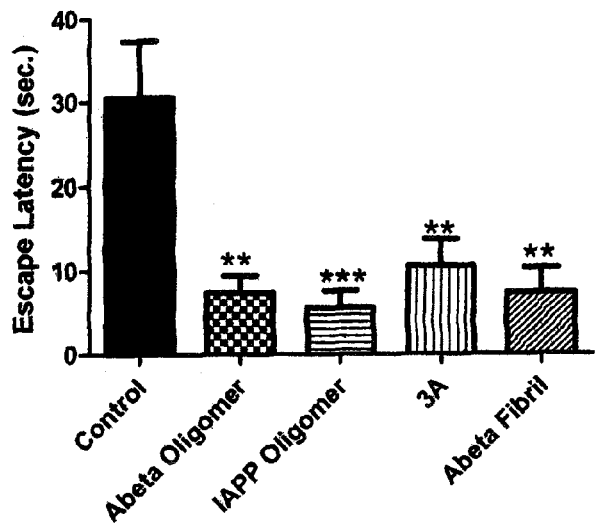
FIG. 6A is a bar graph showing escape latency in a Morris Water Maze test of Tg2576 mice following control or test vaccinations, as described in Example 7 below.
Figure 6B:
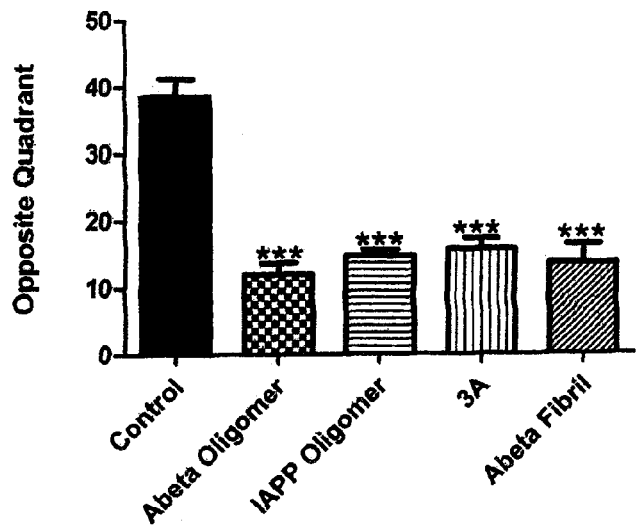
FIG. 6B is a bar graph showing time spent in the opposite quadrant after platform removal in a Morris Water Maze test of Tg2576 mice following control or test vaccinations, as described in Example 7 below.
Figure 6C:
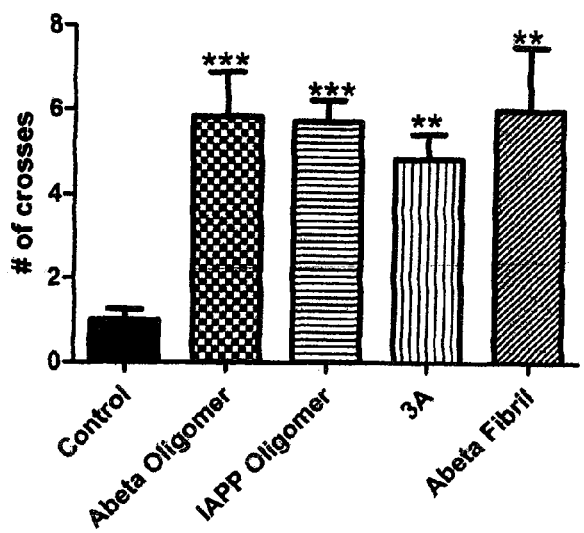
FIG. 6C is a bar graph showing number of crosses in a Morris Water Maze test of Tg2576 mice following control or test vaccinations, as described in Example 7 below.

In the Morris Water Maze test, Tg2576 mice that had received six (6) monthly vaccinations with Aβ oligomer and IAPP oligomer demonstrated significantly improved acquisition and retention capabilities, indicating improved special memory related with hippocampus compared to controls. Specifically, FIGS. 6A-6C show results of the 24 hour Morris Water Maze test at the 14 month time point. The mice vaccinated with Aβ oligomer, IAPP oligomer, 3A peptide and Aβ fibrils show significant improvement in retention memory on the escape latency to cross the platform location (FIG. 6A), number of platform crosses (FIG. 6B) and time spent in opposite quadrant (FIG. 6C), during the 24 hr test period, as compared to control-vaccinated mice.

Object Recognition Study-Results

Figure 7:
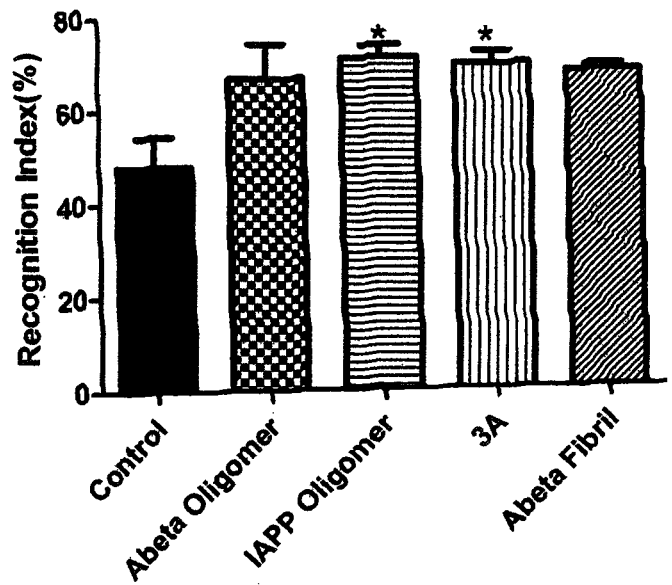
FIG. 7 is a bar graph showing familiar object recognition indices (RI) determined in an object recognition study of Tg2576 mice following control or test vaccinations, as described in Example 7 below.

FIG. 7 shows the recognition index (RI) for each treatment group. The RI is the percentage of time spent exploring the novel object as opposed to the familiar object. As seen in FIG. 7, at 6 months, the RIs for IAPP oligomer-vaccinated mice and 3A peptide-vaccinated mice were significantly higher than the RIs of control mice, thereby indicating that, at 6 months post-treatment, mice that had been vaccinated with the IAPP oligomer and 3A peptide demonstrated significantly better object recognition than unvaccinated controls.

Passive Avoidance Study-Results

Figure 8:
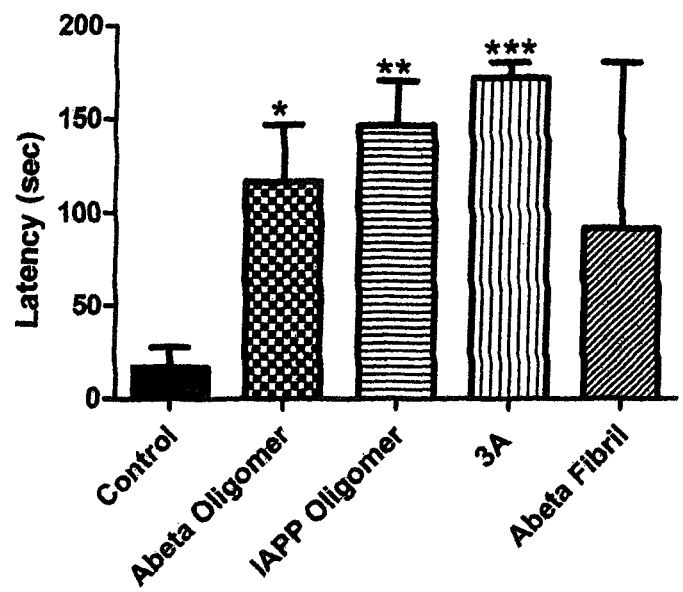
FIG. 8 is a bar graph showing passive avoidance memory retention (mean latency±S.E.M.) in an electroshock passive avoidance study of Tg2576 mice following control or test vaccinations, as described in Example 7 below.

FIG. 8 shows Results of the passive avoidance study. In this study, contextual learning and memory was evaluated using the passive inhibitory avoidance task. Passive avoidance memory retention (mean latency±S.E.M.) was measured as a function of each animal's ability to remember an electrical shock at 90 minutes and 24 hours following shock administration in Tg2576 mice (14 months). The mice vaccinated with Aβ oligomer, IAPP oligomer and 3A peptide show significant improvement as compared to control vaccinated mice. This test depends on amygdala.

CONCLUSIONS

Vaccination against generic amyloid oligomer epitopes is effective to attenuate cognitive impairment and amyloid Aβ sequence is not necessary to produce a protective immune response. Thus, vaccination against a non-human amyloid oligomer epitope is a potentially efficacious vaccine strategy that would not have the potential for autoinflammatory immune complications.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A composition comprising a modified or unmodified synthetic peptide or epitope comprising a fusion protein having an amino acid sequence joined to a surface of a particle, film or sheet in a manner which causes the peptide or epitope to be constrained in a conformation that allows it to a) bind an antibody that selectively or specifically binds to a prefibrillar aggregate comprising a naturally occurring amyloid peptide without binding substantially to monomers or fibrils of the amyloid peptide or b) induce production in a mammal of an antibody that selectively or specifically binds to a prefibrillar aggregate comprising a naturally occurring amyloid peptide without binding substantially to monomers or fibrils of the amyloid peptide, wherein the peptide or epitope comprises alternating polar and non-polar amino acid residues and the surface of the particle, film or sheet comprises a material selected from the group consisting of gold, zinc, cadmium, tin, titanium, silver, selenium, gallium, indium, arsenic, silicon, mixtures thereof and combinations thereof.

2. A composition according to claim 1 wherein said fusion protein comprises an antigenically effective portion of a carrier protein.

3. A composition according to claim 1 wherein said fusion protein comprises a carrier protein selected from the group consisting of a serum albumin, an immunoglobulin molecule, thyroglobulin, ovalbumin, a toxoid, a cytokine, a chemokine and a transmembrane transport protein.

4. A composition according to claim 1 wherein said composition comprises an adjuvant.

5. A composition according to claim 4 wherein the adjuvant comprises an aluminum salt.

6. A composition according to claim 4 wherein said adjuvant comprises an oil-in-water emulsion.

7. A composition according to claim 1 wherein the surface of the particle, film or sheet comprises gold.

8. A composition according to claim 1 wherein the particle, film or sheet comprises a gold microsphere.

9. A composition comprising SEQ ID NO: 10.

10. A composition comprising SEQ ID NO: 11.

11. A composition comprising SEQ ID NO: 12.

12. A composition comprising SEQ ID NO: 13.

* * * * *